(12) United States Patent
Tam et al.

(10) Patent No.: US 7,029,628 B2
(45) Date of Patent: Apr. 18, 2006

(54) PORTABLE CO-OXIMETER

(75) Inventors: Lisa A. Tam, Lake Forest, CA (US); James Huntington Dabney, Irvine, CA (US); Michael H. Burnam, Calabasas, CA (US); Martin J. Patko, Anaheim Hills, CA (US)

(73) Assignee: Stat-Chem Inc., Orange, CA (US)

( * ) Notice: Subject to any disclaimer, the term of this patent is extended or adjusted under 35 U.S.C. 154(b) by 385 days.

(21) Appl. No.: 09/752,502

(22) Filed: Dec. 28, 2000

(65) Prior Publication Data

US 2002/0086432 A1    Jul. 4, 2002

(51) Int. Cl.
*G01N 33/00* (2006.01)
(52) U.S. Cl. .................................. 422/68.1; 422/82.05
(58) Field of Classification Search ............... 422/68.1, 422/82.05
See application file for complete search history.

(56) References Cited

U.S. PATENT DOCUMENTS

| | | | |
|---|---|---|---|
| 4,003,662 A * | 1/1977 | Retzer et al. ............... 356/435 |
| 4,744,656 A | 5/1988 | Moran et al. | |
| 4,776,340 A | 10/1988 | Moran et al. | |
| D337,388 S | 7/1993 | Nilsson et al. | |
| 5,277,181 A | 1/1994 | Mendelson et al. | |
| 5,372,135 A | 12/1994 | Mendelson et al. | |
| 5,567,869 A * | 10/1996 | Hauch et al. ............... 73/64.41 |
| 6,084,661 A | 7/2000 | Mendelson et al. | |
| 6,103,197 A | 8/2000 | Werner | |
| 6,379,969 B1 * | 4/2002 | Mauze et al. .................. 436/68 |
| 6,638,769 B1 * | 10/2003 | Lilja et al. ..................... 436/66 |

FOREIGN PATENT DOCUMENTS

| | | |
|---|---|---|
| EP | 0 821 784 B1 | 11/1998 |
| WO | WO 98/33399 | 10/1996 |
| WO | WO 99/18422 | 4/1999 |
| WO | WO 99/36765 | 7/1999 |
| WO | WO 00/33063 | 6/2000 |

OTHER PUBLICATIONS

Zwart, et al., *Results of Routine Determination of Clinically Significant Hemoglobin Derivatives by Multicomponent Analysis* (Clinical Chemistry, vol. 32, No. 6, 1986).

* cited by examiner

*Primary Examiner*—Monique T. Cole
(74) *Attorney, Agent, or Firm*—Curtis L. Harrington

(57) ABSTRACT

The invention discloses a system, method and medical device for measuring various hemoglobin derivatives, such as oxyhemoglobin, reduced hemoglobin, partial hemoglobin, carboxyhemoglobin, methemoglobin and sulfhemoglobin in whole or in hemolyzed blood. The novel method uses a statistical approach to enable the design of a portable co-oximeter. This portable co-oximeter utilizes compact light sources, such as light emitting diodes or light emitting lasers, to emit light in the visible region. Being portable, the device is a point-of-care device that can be used in emergency situations by paramedics, in the emergency room, and in a physicians office to detect and measure the concentrations and/or percentages of functional and non-functional hemoglobin derivatives in a patient's blood.

23 Claims, 16 Drawing Sheets

Real LED Weighted

Figure legend read from top to bottom of the graph corresponds to bars of graphs starting from left to right for each hemoglobin form O2Hb Figure legend read from top to bottom of the graph corresponds to bars of graphs starting from left to right for each hemoglobin form

PORTABLE CO-OXIMETER

BACKGROUND

Hemoglobin derivatives are an important clinical parameter for diagnosis of the oxygen carrying capability of blood hemoglobin. The functional hemoglobin derivatives are known as oxygenated hemoglobin ($O_2Hb$) and deoxy- or reduced hemoglobin (rHb). In many cases, the presence of other, non-functional hemoglobin derivatives, such as carboxyhemoglobin (COHb), methemoglobin (metHb) and/or sulphhemoglobin (sHb) may affect the measurement and/or calculation of oxygen-related parameters, such as oxygen saturation. Indeed, information regarding the presence of other hemoglobin derivatives is important, as these derivatives are non-functional, i.e., they do not have any significant capability to carry oxygen.

Traditionally, hemoglobin derivative measurements are performed using hemoglobin analyzers known as co-oximeters. Current models of tabletop co-oximeters use various numbers of wavelengths to measure and distinguish various hemoglobin derivatives. Some examples of these are the Radiometer ABL700 Series (manufactured by Radiometer Medical A/S, DK-2700 Bronshoj) using128 wavelengths, the AVL912 CO-OXYLITE (manufactured by AVL Scientific Corporation), which is one of the few co-oximeters that measures sHb, uses 17 wavelengths. The AVL912 utilizes a modified spectrophotometer in bandwidths of 6 to 10 nm. The ABL700 uses a typical high-resolution spectrophotometer with a 1½nm bandwidth. The type of technology utilized in the ABL700, and other co-oximeters as well, entails large and highly controlled optical components which results in the tabletop instrument weighing about 75 pounds. In addition, both the AVL912 and ABL700 ultrasonically lyse the red blood cells (RBC) to measure released hemoglobin in plasma. This ultrasonic portion of the system adds size and power requirements to the overall device.

Despite the presence in the art of these large co-oximeters, there is a need, for a point-of-care co-oximeter that is smaller and portable. Such a co-oximeter would enable the direct measurement of functional and/or non-functional hemoglobin derivatives by paramedics, doctors and other health care providers, in the field, in the emergency room or in the medical office.

SUMMARY

In accordance with the invention, an optical device for measurement of hemoglobin derivatives including and not limited to oxygenated hemoglobin, deoxy-hemoglobin, carboxyhemoglobin, methemoglobin and sulphhemoglobin is described. The measurement may take place on diluted and undiluted, hemolyzed or non-hemolyzed blood, and at room or body temperature. This device has several advantages over the current co-oximeters in that it is compact, portable, and may be battery operated.

Also, in accordance with the invention, the portable co-oximeter utilizes reduced size optical components, such as light emitting diodes (LEDs). LEDs are available in various sizes, bandwidths and peak wavelengths.

Further, the portable co-oximeter of the present invention may be used to measure or calculate hematocrit, and also to calculate total hemoglobin, oxygen saturation ($SaO_2$), fractional oxygen saturation ($SaO_2$frac), oxygen content and oxygen capacity.

In accordance with the invention, another method leading to a reduction in size of the co-oximeter is to take measurements on a whole blood sample, thus eliminating the size and power requirements of currently available lysing devices that accompany prior art co-oximeters. Yet another method for the reduction of the size of the medical device of the invention is to perform the measurements on a blood sample without temperature compensation.

To accomplish the foregoing, a portable system, device and method for measuring/detecting various hemoglobin derivatives in a non-hemolyzed, or hemolyzed, blood sample taken from a patient are provided. The system/device/method comprise subjecting the sample to radiation of at least one wavelength for each hemoglobin derivative to be measured, $\lambda_1, \lambda_2, \lambda_3, \lambda_4 \ldots \lambda_n$ where n is defined as the number of desired hemoglobin derivatives. However, when using whole blood, non-hemolyzed samples, an additional wavelength is needed for adjustment of turbidity resulting from the presence of intact red blood cells in the non-hemolyzed blood sample. Thus, for a whole blood non-hemolyzed sample the sample is subjected to radiation at n+1 wavelengths for all hemoglobin derivatives of interest.

In accordance with the invention, a measurement of absorbance, transmittance or reflectance may be used to perform the measurement of hemoglobin derivative. These determined values further may be used to measure the hematocrit of the non-hemolyzed sample. Reflectance may be used when measuring whole blood due to the scattering effects of the cell walls of the red blood cells.

Generally, in the system, device and method of the invention, the absorbance and/or reflectance of the blood sample at each wavelength is measured, and then this measured value is used to solve for the concentration and/or percentage of each hemoglobin derivative of interest. This method is readily described in the literature, e.g., Zwart, et al. (Clinical Chemistry, Vol. 32, No. 6, 1986) and is incorporated herein by reference in its entirety.

One embodiment of the invention utilizes compact light sources with bandwidths in the range of 7–100 nm without the use of narrow bandwidth bandpass filters and/or complex diffraction gratings. Another embodiment can utilize a compact broadband light source with bandpass filters. Still, another embodiment can utilize bandwidth compact light sources in the range of 10–60 nm along with bandpass filters.

Thus, the novel system, device and method are developed to utilize existing and future technology in compact light sources to create a portable co-oximeter. Some examples of the type of light sources suitable for use in the present invention include, but are not limited to, light emitting diodes, laser diodes or small monochromatic light sources. Monochromatic light sources, as well as light emitting diodes and laser diodes are readily available in various wavelengths of light, sizes, intensities and power requirements. Heretofore, the difficulty in using compact light sources for the measurement of hemoglobin derivatives was that differentiating between the optical characteristics of the various hemoglobin derivatives heretofore required the use of tightly controlled diffraction gratings or very narrow bandwidth bandpass filters due to the overlapping visible absorption spectra of the various hemoglobin derivatives. This difficulty is now overcome by the present invention.

BRIEF DESCRIPTION OF THE DRAWINGS

The foregoing and other objects, features and advantages of the invention will be apparent from the following more particular description of preferred embodiments of the invention. As illustrated in the accompanying drawing in which like reference characters refer to the same parts throughout the different views. The drawings are not necessarily to scale, emphasis instead being placed upon illustrating the principles of the invention.

FIG. 5 also represents the results for various hemoglobin derivatives using whole bovine blood. In addition, results from the AVL912 Co-Oxylite using 17 distinct wavelengths is charted along with the results for various hemoglobin derivatives using five distinct wavelengths taken from the spectra generated in FIG. 1 at 2 nm bandwidths and the measurements from an HP8541A spectrophotometer.

FIG. 6 also represents the results for various hemoglobin derivatives using whole bovine blood. In addition, results from the AVL912 Co-Oxylite using 17 distinct wavelengths is charted along with the results for various hemoglobin derivatives using five distinct wavelengths in the same manner as in FIG. 5.

DESCRIPTION

I. Developing Methodology of the Invention

The starting point for the development of the system, device and method used to measure the presence of various hemoglobin derivatives is the use of small readily available light sources. For the sake of clarity LEDs will be used as the light source with the understanding that laser diodes and monochromatic light sources, as well as LEDs in combination with bandpass filters or bandpass filters in combination with broadband light sources may be used. When referring to a light receiving source, photodetectors will be used with the understanding that photo transistors, photo diodes, PIN diodes, CCD arrays, photo multipliers and the like may be used.

LEDs are available in various peak wavelengths and bandwidths. A statistical evaluation is typically performed by the manufacturer to describe or specify the LED light source, and these characteristics of LEDs are often used in the evaluation of test data when verifying a product against its performance specification. This type of evaluation is also performed to describe the performance of a bandpass filter. An example of a LED characteristic output may be described as a peak wavelength of 612 nm, for example, with a 50% intensity bandwidth or center wavelength (CWL) of 12 nm. The output of this specific LED may be described by a $3_{rd}$ order polynomial with 98% confidence along a 12 nm bandwidth.

In the present invention an evaluational statistical approach was taken to develop a methodology that enables the use of larger bandwidth light sources, such as LEDs for instance, for use in a portable co-oximeter.

Figure 1:
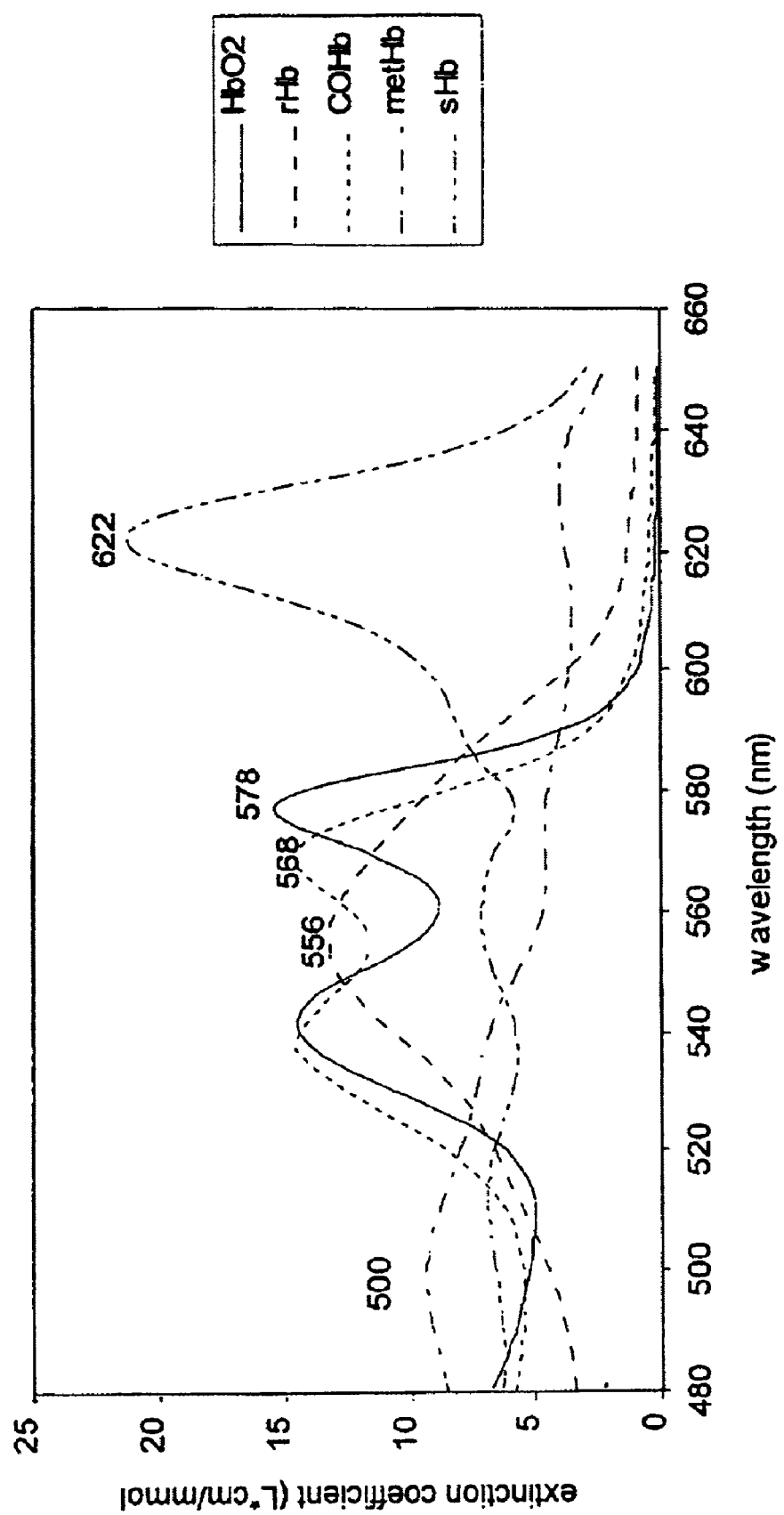
FIG. 1 represents a spectral of various hemoglobin derivative plots empirically obtained by Zwart, et al. (Clinical Chemistry, Vol. 32, No. 6, 1986) illustrating optical absorbance spectra of $O_2Hb$, rHb, COHb, metHb and sHb in the visible wavelength range. This data is plotted in 2 nm bandwidth increments.
Figure 2:
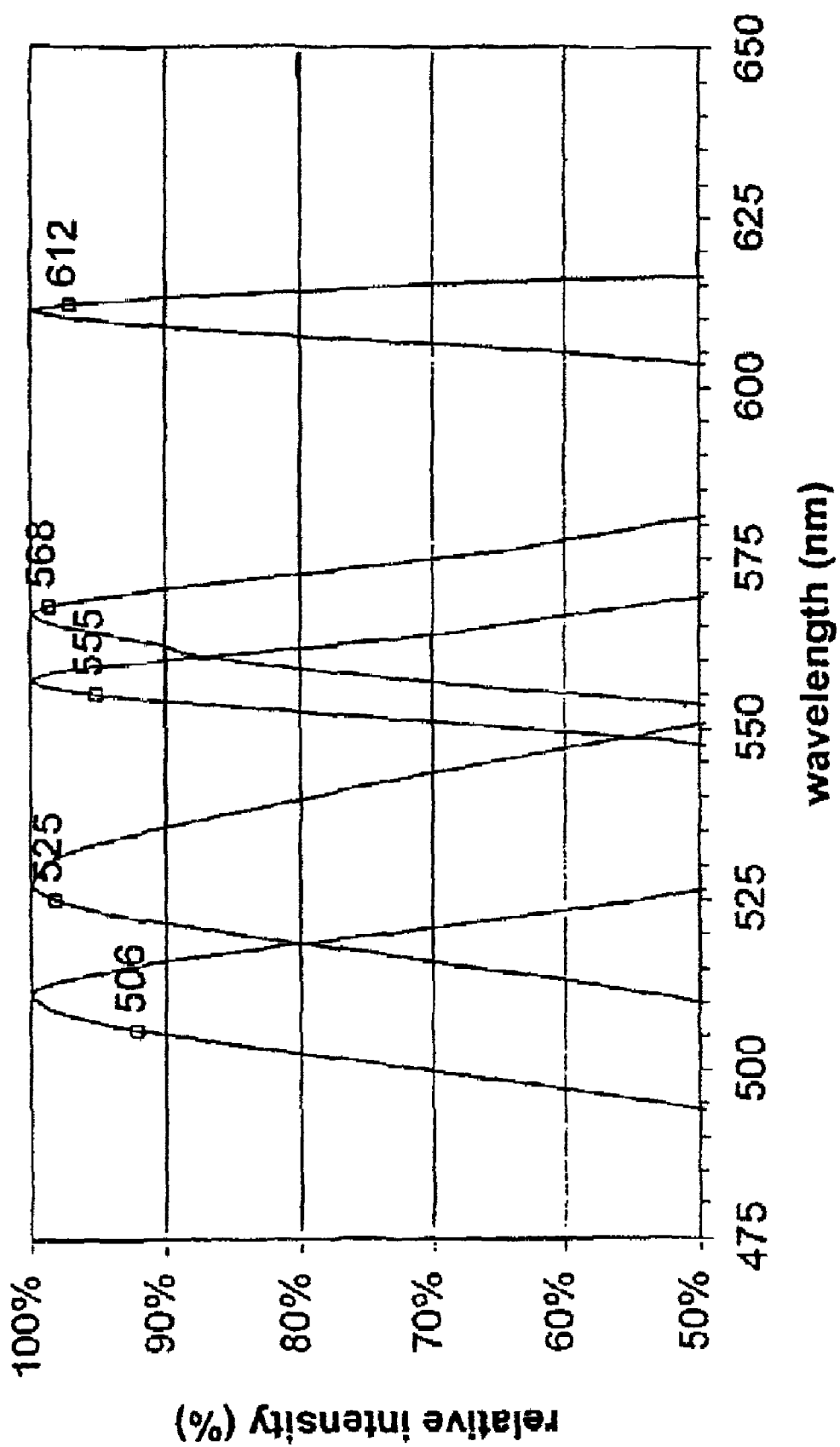
FIG. 2 shows representative output spectra for typical LED light sources in the visible region of the electromagnetic spectrum. The bandwidths (center wavelength) range from 12–36 nm.

As a starting point in the invention, consideration is given to the shape of the curves developed in FIG. 1, as well as the maxima in wavelengths and extinction coefficients of the various derivatives. This is the starting point of the methodology that enables the use of compact light sources in the portable co-oximeter of the invention. In this method, it is assumed that the typical, and probably the worst case LED may be described by a peak wavelength with a 50% intensity bandwidth or center wavelength (CWL) of 40 nm. Thus, 99% of the 50% and greater intensity output of the LED is within 20 nm above the peak and 20 nm below the peak wavelength. FIG. 2 shows examples of the output spectra of typical LEDs in the 12–36 nm range provided by a supplier.

Figure 3:
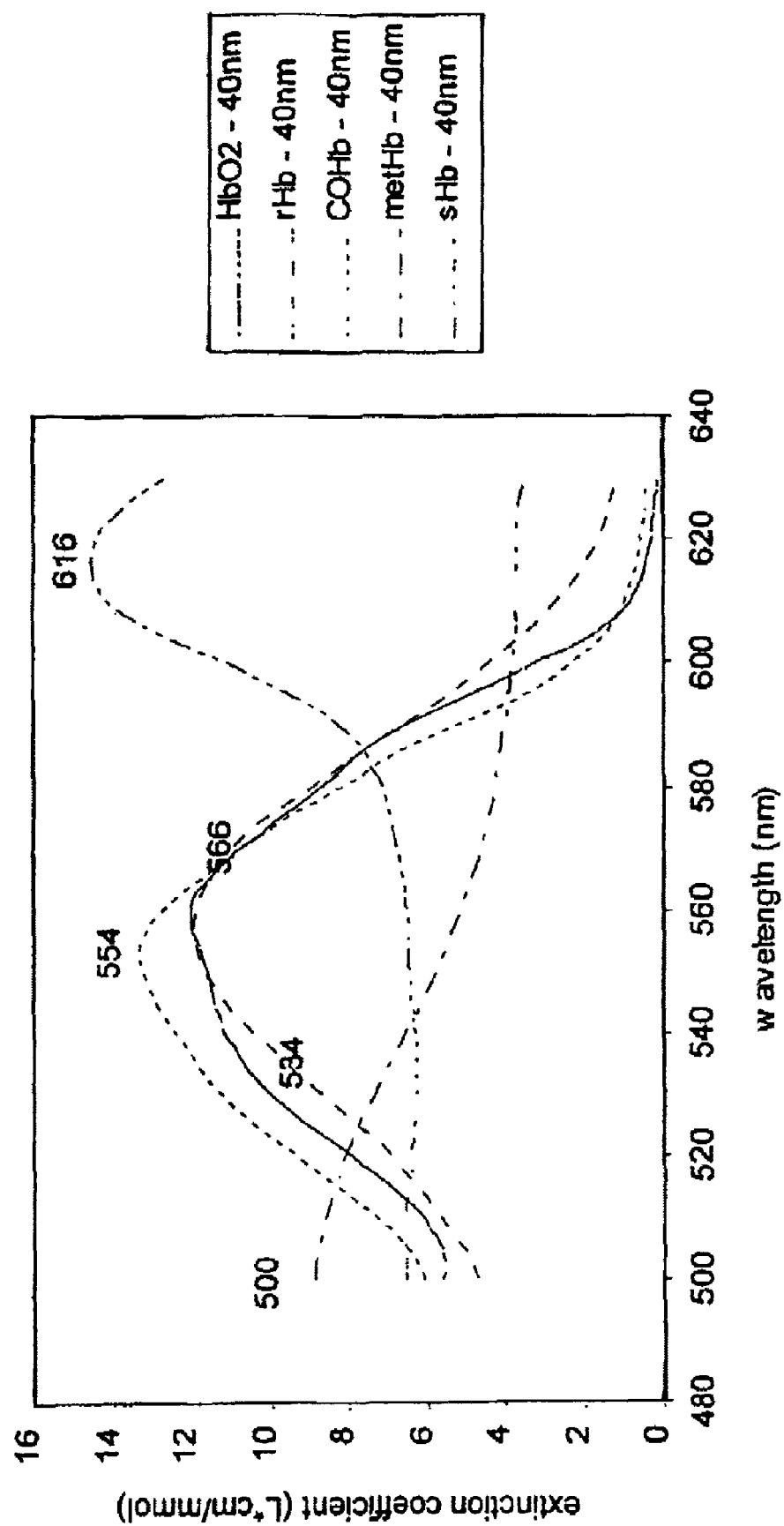
FIG. 3 is a plot of the calculated absorbance spectra of $O_2Hb$, rHb, COHb, metHb and sHb in the visible wavelength range, which essentially represents a superimposition of theoretical 40 nm bandwidth LEDs of peak wavelengths as labeled.

FIG. 3 is a description of the calculated optical behavior of hemoglobin derivatives where the output spectrum of a 40 nm bandwidth LED essentially has been superimposed onto the spectra described in FIG. 1. In essence, the data shown in FIG. 3, represent the empirical data shown in FIG. 1, where data points are generated at every 2 nm, averaged across 40 nm surrounding each peak of interest. Specifically, each data point shown in FIG. 3 was developed by taking a weighted average of 20 data points (a data point at every 2 nm across 40 nm). For example, in order to get a data point at 500 nm, the average was taken across the wavelength range of 480 nm to 520 nm with 500 nm being given the maximum weight. A typical arithmetic average may be performed by adding all 20 data points and dividing the sum by 20. In order to more closely estimate the performance of a typical LED light source with a 40 nm bandwidth, the curves were weighted based on the typical spectral response of a 40 nm light source.

It is noteworthy that the calculated spectra depicted in FIG. 3 show greatly differing maxima and isobestic points as compared to those of FIG. 1. For example, the dual peak maxima of the $O_2Hb$ residing at 542 nm and 576 nm normalizes into a single peak at about 560 nm. Interestingly, the normalization of the rHb may be described very similarly with a single maxima at about 556 nm. It is interesting to note, however, that the normalized plots of these two derivatives and that of COHb, show greatly differing absorption coefficients at about 534 nm. This wavelength has not been considered in any literature reference as a potential measuring wavelength. Thus, from the inventive methodology, different maxima and isobestic points are revealed in FIG. 3 which can be used as measuring wavelengths to determine the concentration and/or percentage of the hemoglobin derivatives of interest using compact light sources, such as LED light sources.

After determining the absorbance of the light generated from a typical LED for the hemoglobin derivatives of interest, simultaneous, or near simultaneous, linear equations are used to calculate the concentration of each hemoglobin derivative. The sum of these concentrations are calculated and reported as total hemoglobin. From this total, the percentage of each hemoglobin derivative can be calculated along with other clinically relevant parameters, such as saturation ($SaO_2$), fractional oxygen saturation ($SaO_2$frac), oxygen content and oxygen capacity.

For greater accuracy in these measured values, a ratio of the absorbance at certain specified wavelengths can be performed, called a ratiometric calculation, to yield more precise values with respect to the percentages of each hemoglobin derivative, as these percentages relate to the total hemoglobin content. Finally, a measurement of the absorbance and/or reflectance of a turbid, non-hemolyzed blood sample at wavelengths in the high visible to near infra red region of the spectrum is taken to adjust for turbidity and to measure the hematocrit of the blood sample.

In addition, the relationship between total hemoglobin and hematocrit may also be used to validate the measurement of total hemoglobin, e.g., hematocrit is equal to 3 times the total hemoglobin in g/dL in non-hemolyzed blood, except in diabetic coma in hyperlipidemia and altered viscosity, as well as other states where the 1:3 relationship for hematocrit is invalid.

The hematocrit also may be measured ratiometrically to bring the measurement into even greater accuracy. Ratiometric calculations improve accuracy particularly for embodiments of the medical devices of the present invention which do not include a thermal device to compensate for temperature effects. Ratiometric calculations also compensate for other environmental effects such as flow rate, presence of air, etc.

From the plots shown in FIG. 1, the peak wavelengths $\lambda_1$, $\lambda_2$, $\lambda_3$, $\lambda_4$ ... $\lambda_n$ are about 500, 556, 568, 578, and 622 nm with a 2 nm bandwidth for each hemoglobin derivative of interest, namely $O_2Hb$, rHb, COHb, sHb and metHb. For the experimental work leading to the invention, 722 nm was chosen as the excitation wavelength for the adjustment for turbidity with a 2 nm bandwidth. The absorbances and/or reflectances at each wavelength are then determined substantially simultaneously using broadband light split into 2 nm bandwidths using a diffraction grating.

Alternatively, from the data developed in FIG. 3, the optimal wavelengths $\lambda_1$, $\lambda_2$, $\lambda_3$, $\lambda_4$ ... $\lambda_n$ are about 500, 536, 554, 566, 616, and 722 nm for measurement of turbidity, using a typical LED with a 40 nm bandwidth. These wavelengths represent the shifts of the optical absorbance spectra resulting from the spectral output of a LED, along a bandwidth of 40 nm.

Figure 4:
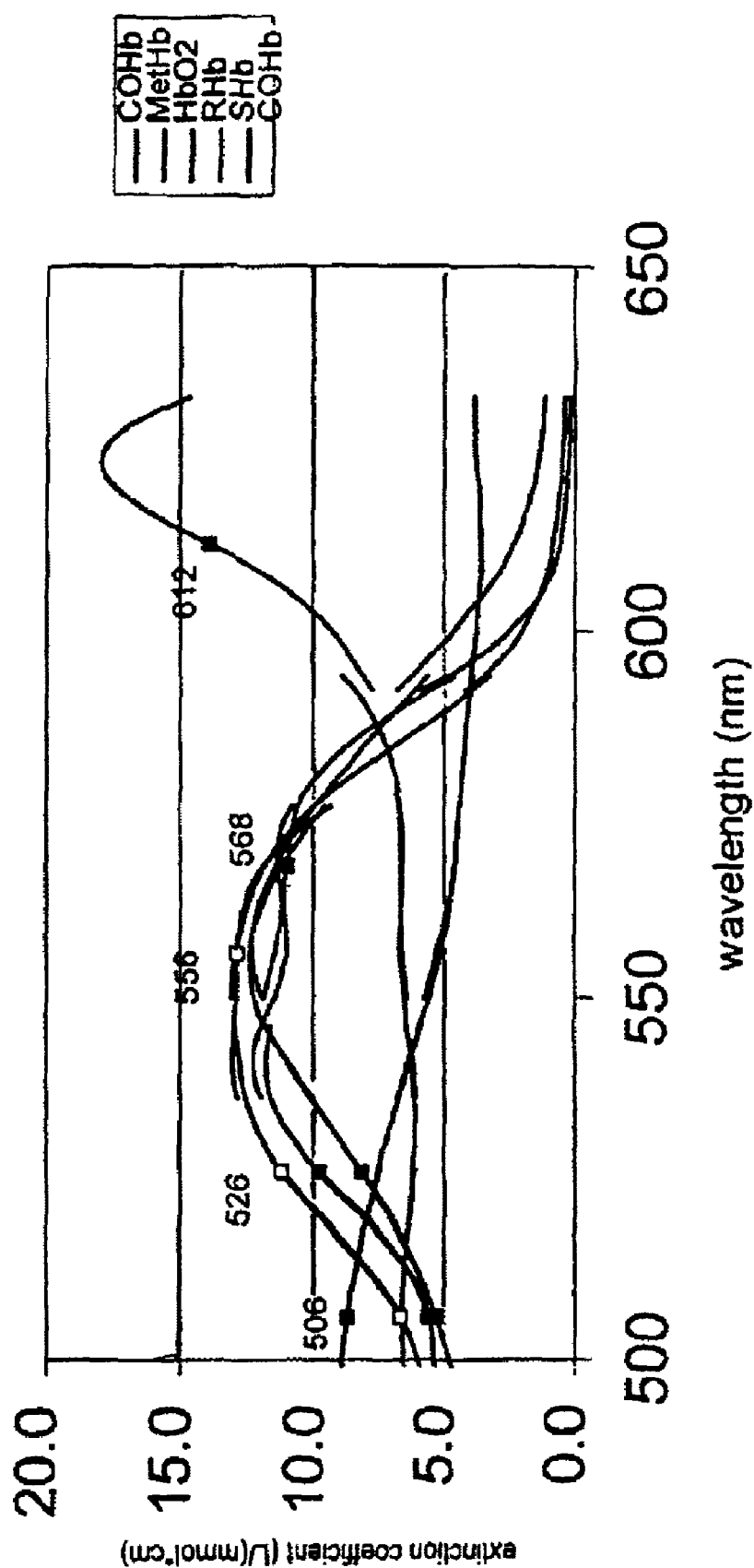
FIG. 4 is a plot of the calculated absorbance spectra of $O_2Hb$, rHb, COHb, metHb and sHb which essentially represent a superimposition of actual bandwidth data of LEDs of peak wavelengths as labeled.

FIG. 4 shows the optimal wavelengths $\lambda_1$, $\lambda_2$, $\lambda_3$, $\lambda_4$ ... $\lambda_n$ are about 506, 526, 556, 570, 610 and 800 nm for adjustment of turbidity using a typical LED with a 20 nm bandwidth. The empirical absorbances and/or reflectances at each of these wavelengths may be measured substantially simultaneously, or in an alternating fashion, using light emitting diodes or diode lasers operable at these wavelengths It is noteworthy that in the invention the optimal wavelengths may be chosen by inspection of the calculated absorption spectrum generated for a given light source. The optimal measuring wavelength, or wavelengths, are those wavelength(s) capable of best distinguishing each hemoglobin derivative of interest. These optimal wavelengths can be determined from the calculated absorption spectra by visual inspection or with the aid of computer software directed to yield the optimal wavelengths for distinguishing among the hemoglobin derivatives. Thus, the optimal wavelengths ultimately will depend on the light source or light sources, or filters selected to be used in an embodiment of the system and device of the invention.

II. Experimental Verification of the Invention

Optical measurements in blood rely on the difference in the optical extinction or absorbance/reflectance coefficient of different hemoglobin derivatives, as illustrated in the plot of FIG. 1. Traditionally, co-oximeters, such as AVL912, utilize a large number of specific wavelengths in the visible region of the optical spectrum. In particular, the AVL912 utilizes 17 wavelengths in the visible region at 530, 536, 542, 548, 554, 560, 566, 572, 578, 584, 590, 604, 612, 622, 630, 640 and 648 nm to measure five hemoglobin derivatives. Selection of the proper wavelengths is achieved by a stepper motor driven monochromator.

The concentrations of oxyhemoglobin ($O_2Hb$), reduced hemoglobin (rHb), carbooxylhemoglobin (COHb), methemoglobin (metHb), and sulphhemoglobin (sHb) may be determined by solving at least five independent equations derived from Beer-Lambert's Law. Beer-Lambert's Law may be described by the following equation:

$$A = \epsilon(\lambda) * c * l.$$

Where

A=absorbance or optical density $\epsilon(\lambda)$=extinction coefficient (L/mmol*cm) at $\lambda$ wavelength (nm)

c=concentration of hemoglobin derivative (mmol/L) and l=pathlength (cm)

These results are expressed in concentration of units of either mmol/L or gram % (g/dL) and in percentage of the tHb, calculated from division by the sum of each individual hemoglobin derivative. Oxygen saturation ($SaO_2$), fractional oxygen saturation ($SaO_2$frac), oxygen content and oxygen capacity may be calculated by the following equations: $SaO_2=[O_2Hb/O_2Hb+rHb)]*100\%$, $SaO_2frac=[O_2Hb/THb]*100\%$, oxygen content=$O_2Hb$, oxygen capacity=$O_2Hb+rHb$.

In selecting suitable light sources for the portable co-oximeter of the invention, light emitting diodes (LED) were considered as the compact light source. Light emitting diodes are available in various peak wavelengths, bandwidths and cost. They are available in small packages that are smaller in size compared to any diffraction grating associated with a broadband light source. The HP8541A spectrophotometer (manufactured by Hewlett-Packard now Agilent Technologies) was used for the initial experimentation, which utilized a diffraction grating that splits polychromatic light into 2 nm bandwidths.

Figure 5:
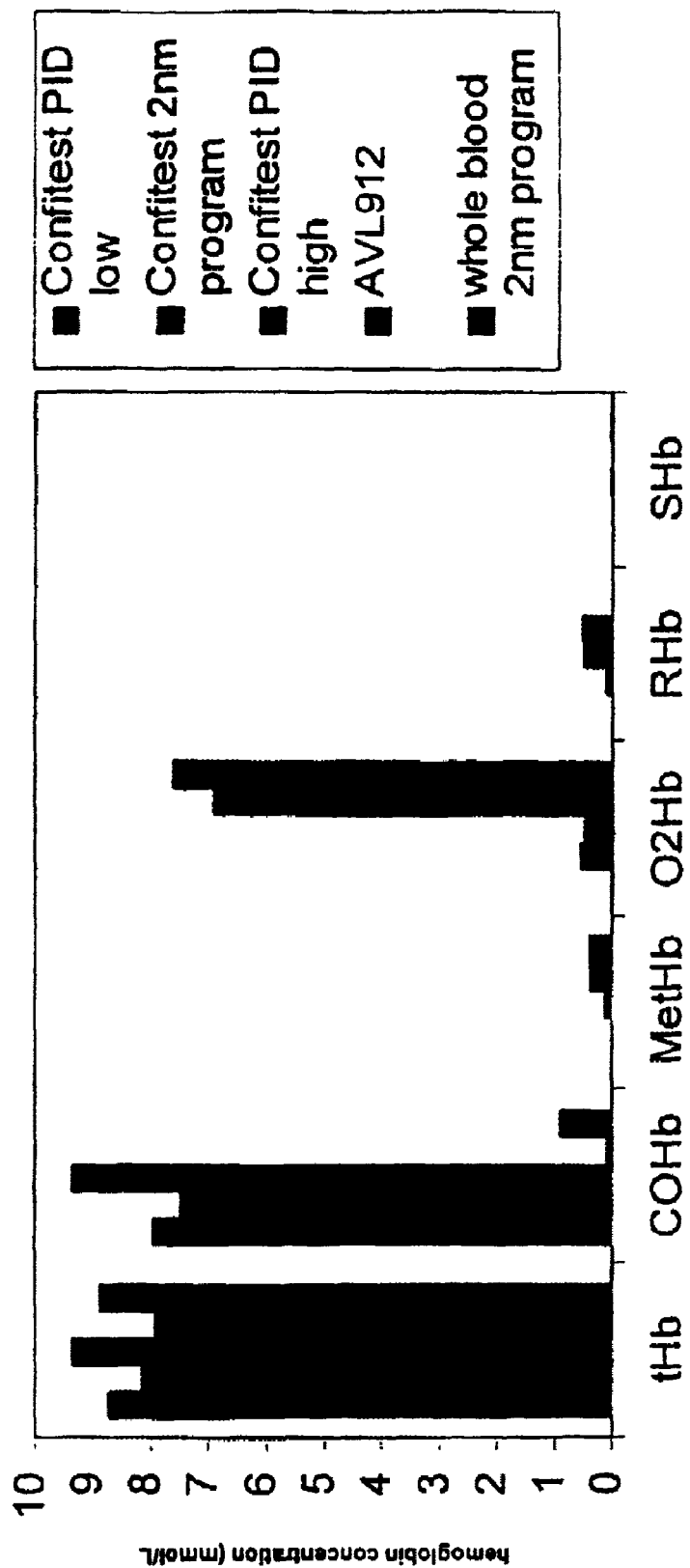
FIG. 5 is a representation of the results for measurements of various hemoglobin derivatives using AVL Confitest ff™ solutions, which are standardized solutions that mimic the behavior of the various hemoglobin derivatives. Results from the product insert range for each hemoglobin species is charted along with the results using five distinct wavelengths taken from the spectra generated in FIG. 1 at 2 nm bandwidths using an HP8541A spectrophotometer.

To develop the system, device and method of the present invention, standard quality control liquids were used. AVL provides three levels of QC liquids, Confitest 1, 2 and 3 resulting in similar percentages of each hemoglobin derivative but at different total hemoglobin levels. These standard solutions are used in conjunction with the AVL912 CO-oximeter and compared with the product insert and the printed result for the AVL912 instrument. In addition, absorbance measurements were performed with an HP8541A spectrophotometer, and placed into equations of the Beer-Lambert Law for calculations of hemoglobin concentrations. The results with whole blood compared with the results from the AVL912 and are shown in FIG. 5.

One important challenge that LEDs present are realized in their spectral emission. The emission of a LED is specified as its peak wavelength and bandwidth. The bandwidth of the emission of a LED is a major component in the cost of the LED. An important aspect of the reduction in size is the determination of potential bandwidths that may prove to be feasible to distinguish between the various hemoglobin derivatives, as many of the derivatives have similar and overlapping optical spectra.

The extinction coefficients of each of the hemoglobin derivatives were normalized among a 40 nm bandwidth and the resulting plot is shown in FIG. 3. The results depicted in FIG. 3 were obtained by normalizing the absorption coefficients of each of the hemoglobin derivatives across the wavelength spectrum. The normalization used can be described as a normal distribution across a 40 nm wide bandwidth including 3 standard deviations. Five wavelengths were used in the solution of the Beer-Lambert Law for the five hemoglobin derivatives of interest. As discussed above, the output weighting equation taken along 40 nm shifted the spectra some and therefore the maxima of the $O_2Hb$ shifted from a dual peak at 542 nm and 576 nm to a single maxima at 560 nm very closely resembling and overlapping the maxima of the rHb at 558 nm. For this reason, a wavelength at about 536 nm was chosen to distinguish between $O_2Hb$ and rHb and also COHb for use with a 40 nm LED light source.

The wavelength at about 536 nm shows a large disparity and significant amplitude in the optical spectra of the $O_2Hb$, rHb and COHb. The lowest amplitude is expressed in the spectra of rHb where the extinction coefficient is about 7.97 which is much greater than those in the near infrared, where the extinction coefficient is about 0.3. The wavelength at about 566 nm is representative of an isobestic point for the three derivatives. The maxima of the COHb shifted from a dual peak at 540 nm and 568 nm to a single maximum at about 554 nm. The maxima of sHb shifts slightly from 622 nm to about 616 nm.

Figure 6:
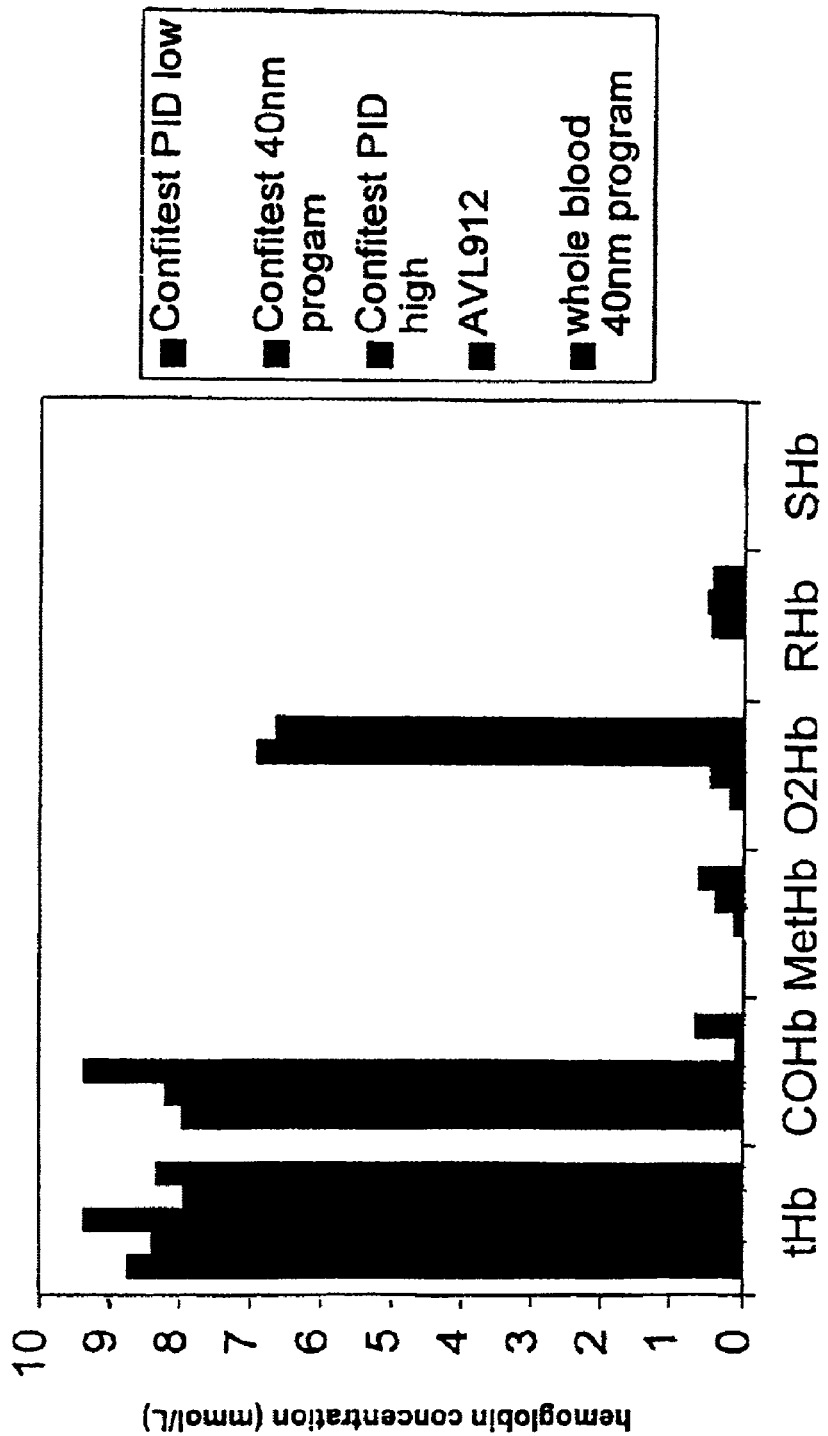
FIG. 6 is a representation of the results for measurements of various hemoglobin derivatives using AVL Confitest ff™ solutions, which are standardized solutions that mimic the behavior of the various hemoglobin derivatives. Results from the product insert range for each hemoglobin species is charted along with the results using five distinct wavelengths taken from the spectra generated in FIG. 3 using the theoretical 40 nm bandwidth LEDs and the measurements from an HP8541A spectrophotometer.

The results with AVL Confitest Quality Control fluids and whole blood are shown in FIG. 6.

The weighted optical spectra among 40 nm was plotted with theoretical various mixtures of $O_2Hb$, rHb and COHb as these derivatives overlap each other in the wavelength ranges of 530–580 nm. In this example, the contributions of metHb and sHb are minimal.

In order to verify the percentages of $O_2Hb$, rHb and COHb it is assumed that the amounts of MetHb and sHb do not affect the absorbances a high degree in the area of 534 to 566 nm. FIG. 3 shows this to be a valid assumption as even when 100% present, the extinction coefficients are about 50% or less than that of the hemoglobin derivatives of interest. The optical density of each of the wavelengths of 534 nm, 554 nm and 566 nm may be calculated as resulting from only the $O_2Hb$, rHb and COHb by using Beer-Lambert's Law and subtracting the contribution of MetHb and sHb using the measured concentrations from the previous portion of the program.

These calculated absorbances may then be taken as a ratio and related to the percentages of $O_2Hb$, rHb and COHb. The ratiometric measurement has an advantage in that environmental factors may similarly affect absorbances in similar manners and may be cancelled out when taking the ratio. Some examples of these environmental factors are, but are not limited to temperature, pH, hematocrit, air bubbles, cuvette factors, etc.

After the absorbances and calculated concentrations and percentages of the five hemoglobin derivatives are obtained, ratiometric curves may be used to validate and/or fine tune the percentages of hemoglobin derivative. The result can then be mathematically iterated into the original absorbances for adjustment. In this manner, the environmental factors such as temperature, air bubbles and slight disparities in cuvette thickness, pathlength and position may be compensated.

Measurement of turbidity can take place at any wavelength of the visible to near infrared range. The extinction coefficients of the hemoglobin derivatives is about 10 times lower in this wavelength range, and therefore, does not absorb a great amount of light in this wavelength range. It is, therefore, advisable to work in the near infrared wavelength ranges in order to eliminate the sensitivity to hemoglobin type. The verifying experimentation was performed at 722 nm as the HP8451 measures quite adequately at this wavelength. Measurement of turbidity may be used for the adjustment for the presence of the RBC's and may also be used to provide information of the hematocrit. Hematocrit or the volume percent of RBC's in a blood sample is also an important parameter to monitor. The method, system and device of the present invention may also be used to measure hematocrit directly, in addition to permitting the calculation of the hematocrit indirectly based on the sum of all hemoglobin derivatives.

Those well acquainted in the art understand that turbidity and hematocrit are related in the field of blood chemistry and that total hemoglobin is also related to hematocrit. The turbidity relates to the hematocrit in that it is the cell membrane of the red blood cells that effectively scatter light, and therefore, inhibit its transmission of light radiation. Thus, it is important to make an adjustment in absorbance measurements, as it is the light transmission that is measured, while the absorbance is indirectly measured with the assumption that all light that is not transmitted is absorbed from the sample. Absorbance is related to transmission by the relationship of:

$$Abs = \log(100\%/\%T)$$

Where:
  Abs=absorbance
  %T=percent transmittance.

If in fact some of the light is scattered, this mathematical relationship is invalid and scattering must be accounted for. The scattering of red blood cells is similar across the visible and near infrared ranges. It is for this reason that the recommendation of turbidity measurement be performed in the near infrared range.

As discussed above, a method for the reduction in size of the portable co-oximeter is the use of LEDs as the light source. It is assumed for the development that the distribution of the wavelength output is normal around the peak wavelength. Also, as stated above, FIG. 3 is the data of FIG. 1 with a 40 nm bandwidth "filter." This "filtering" of the data was performed with mathematical software. The population of the extinction coefficients of each 2 nm from 480 nm to 650 nm was weighted along 40 nm with an assumed polynomial equation of $3^{rd}$ order. It is assumed that 100% of the output of intensity greater than 50% (CWL) is captured in this equation. A 40 nm bandwidth is representative of current LED sources in the red to near infrared range, and about 20 nm bandwidth is representative for the lower visible wavelengths. It is noted that these bandwidths represent typical values. LEDs are available in tighter bandwidths by selection at a premium price.

FIG. 4 is an example of this same type of weighting taken over a 12–36 nm bandwidth of real or actual LEDs. It may be understood by those in the art that any type of statistical distribution describing the light source may be applied to this data of extinction coefficients and may represent the performance of many types of light sources, including those using bandpass filters and fiberoptics. To develop this plot, five distinct LEDs with associated peak wavelengths are used that are available as off the shelf items. In this case the supplier is the distribution network, PRP Optoelectronics Inc. Data sheets received from PRP Optoelectronics gave about a 12–36 nm bandwidth that may be described by polynomial equations of 93–98% confidence.

FIG. 5 shows a bar graph of the results of the Confitest solutions. These solutions mimic the behavior of COHb only. The product insert included with the Confitest solutions gives a range of expected results that indicate the AVL 912 Co-Oxylite is in calibration. Results from the data of this same fluid measured in the HP8541A and data placed into a proprietary software program using the Beer-Lambert Law gives the results graphed as the second from the left to right bar. Note that the values calculated for this second bar are trending appropriately but somewhat slightly lower than the expected values for PID low and PID high as these related to tHb.

Whole blood was used in addition to the Confitest solutions and also plotted in FIG. 5. In this case, as well the data taken from the HP8541A, trends in the same manner as the AVL912. These deviations are acceptable as the objective was to demonstrate feasibility of measurement and only the five wavelengths specified in FIG. 1 were used. Current devices measure at more wavelengths, e.g., 17–128 wavelengths.

FIG. 6 shows the results of the same Confitest fluid information plotted with the data of the same fluid measured from the HP8541A and proprietary software using the 40 nm filter as described and charted in FIG. 3. Note that the results of the 40 nm program trend with the expected results of the Confitest solutions.

Note that the results for FIG. 6 of the 40 nm program trend with the expected results of the Confitest solutions and also fall within the expected range of the Confitest solutions. Also, in FIG. 6, whole blood was used in addition to the Confitest solutions and trends in the same manner as the AVL912.

Figure 7:
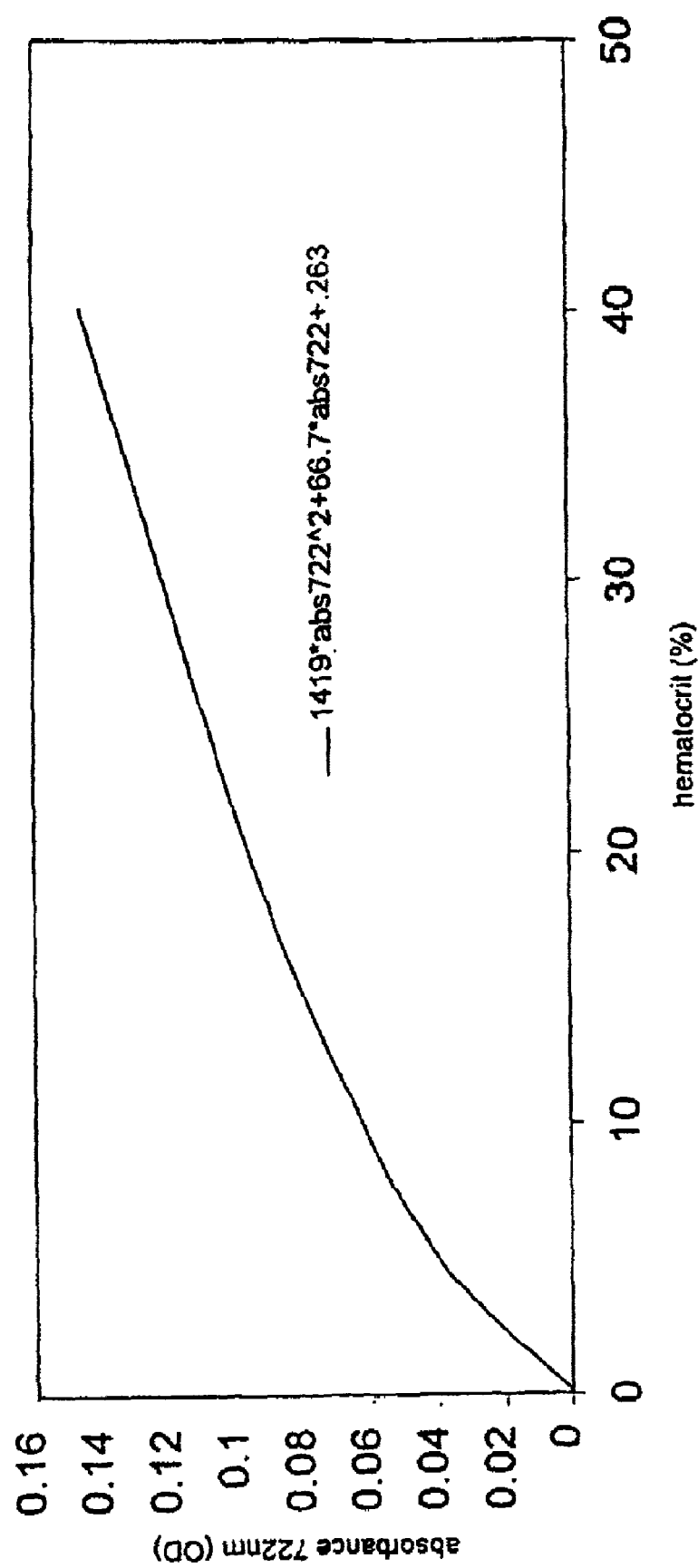
FIG. 7 is a plot of absorbance at 722 nm taken from an HP8541A spectrophotometer vs. hematocrit of whole bovine blood. Wavelengths in the visible range to the near infrared range are similar in shape and can be described by similar equations. 722 nm is plotted here for clarity.

FIG. 7 shows the relationship between the high visible to near infrared wavelength light sources and the mathematical relationship between that and the hematocrit (volume % of red blood cells in a blood sample). A similar equation/relationship exists between any wavelength and bandwidth in this region. It is noteworthy that the extinction coefficients in this wavelength range are on the order of 40 times less than in the low visible wavelength range. Therefore, the absorbance and/or reflectance in this range may be less sensitive to concentration of hemoglobin derivatives. It may also be noted that just as a ratiometric relationship may not be affected by environmental factors, this measurement too may be best expressed as a ratiometric relationship.

Figure 8:
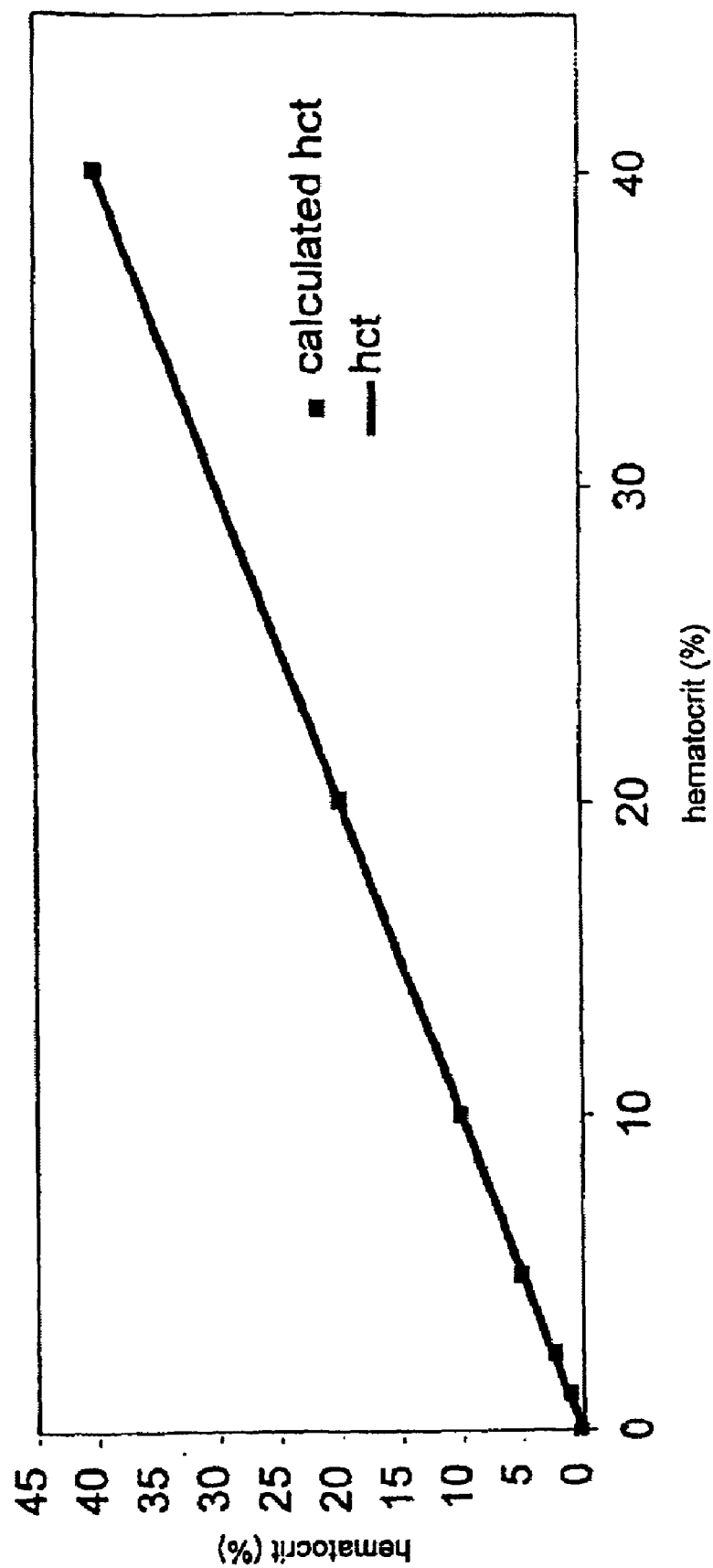
FIG. 8 is a plot of hematocrit vs. calculated hematocrit in the high visible to near infrared wavelengths (722 nm) using whole bovine blood. This information is used for turbidity adjustment for all data presented.

FIG. 8 is a chart of calculated hematocrit from the relationship shown and described in FIG. 7. This figure covers the entire biological hematocrit range. The hematocrit used as the control is the results from the AVL 912 Co-Oxylite total hemoglobin multiplied by 3. This work has also been verified by performing hematocrit measurements using a hematocrit centrifuge.

III. An Example of a System and a Device of the Invention

Figure 9:
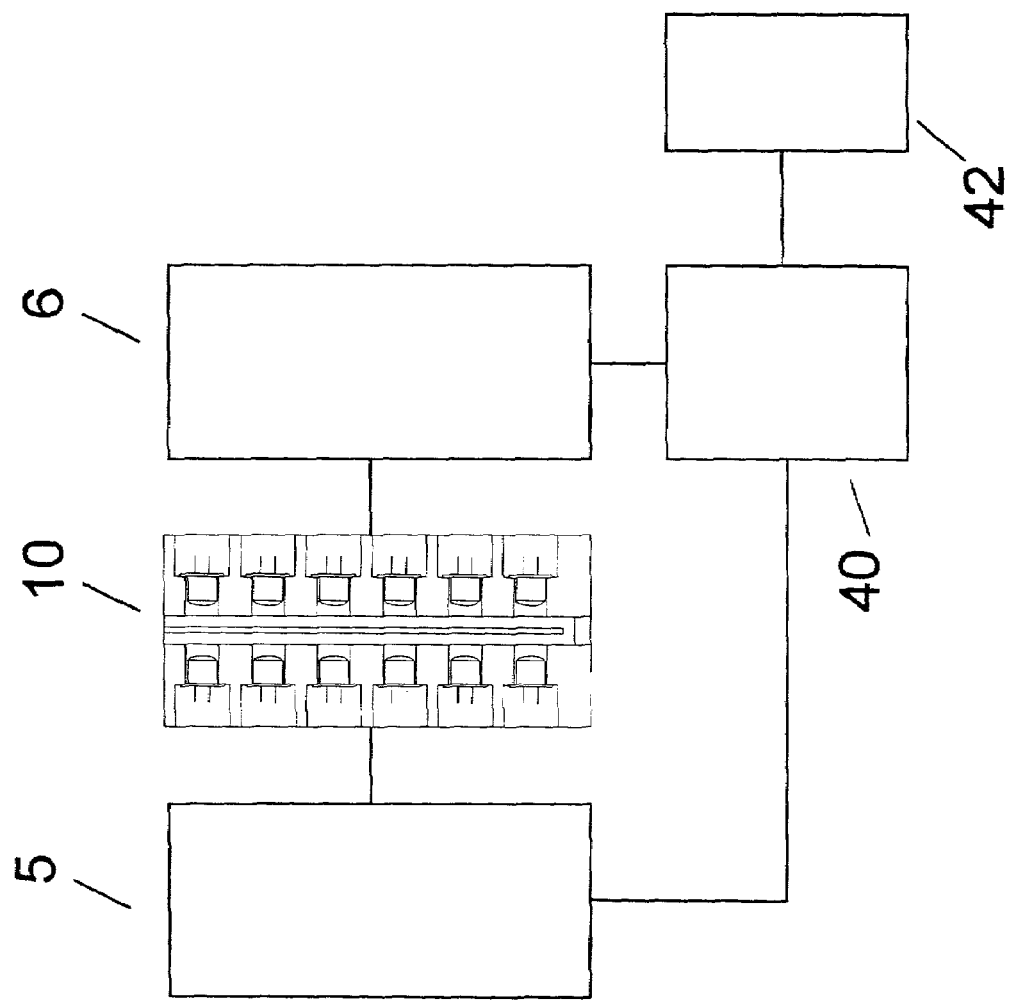
FIG. 9 illustrates a schematic of an embodiment of the system of the present invention.
Figure 10:
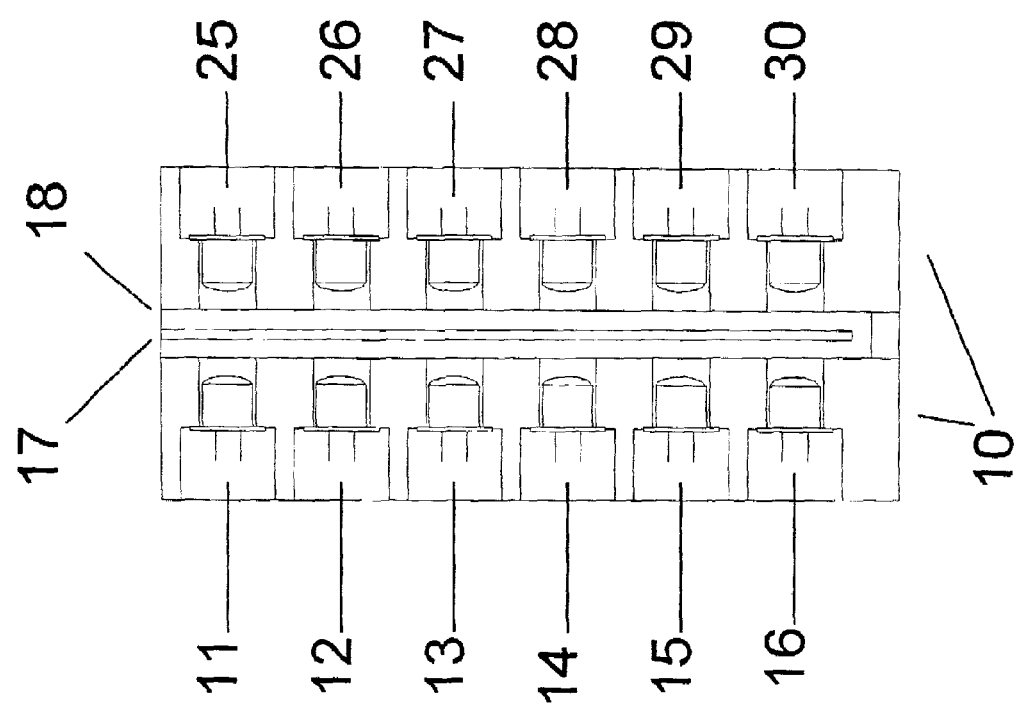
FIG. 10 illustrates an embodiment of the device of the present invention.

FIGS. 9 and 10 illustrates the system and device of the present invention. Functionally, the system is a dedicated purpose spectrophotometer system utilizing a number of fixed wavelength emitters to provide for a means of measuring absorbance of those frequencies. These emitters are optically combined to result in, essentially, a point source emitter capable of any of six available output wavelengths. The emitters are optically coupled though the sample cuvette to a photo detector (PIN diode) and suitable recovery electronics. While a number of different approaches are also possible, a goal is to utilize the approach which also will result in the most cost-effective and reliable product design.

FIG. 9 illustrates a schematic design of the system of the present invention. An emitter is energized at a known output level generating light of specific wavelength(s), which is passed through the sample onto the corresponding detector. The resulting detected current (light) is read by the computer and converted to appropriate units of transmittance, absorbance and/or reflectance. The results are further manipulated in conjunction with the requirements of the application to render results of hemoglobin concentration, % hemoglobin and other results in accordance with the requirements of the application. The schematic shown in FIG. 9 is meant to be illustrative for the use of a multitude of suitable components and product families from which to implement in specific embodiments of the present invention.

The system shown in FIG. 9 is comprised of a processor platform which provides support for a user interface of display and keypad, system control and interface capability to external devices. Interfaced to the control computer are control and data acquisition system devices. These provide selection and control of the light emitters as well as control over the sensitivity of the recovery (detector) system and the ability to convert the detected light to numerical values useful in calculations by the computer. Common to all of these are a power supply system. The following is a detailed discussion of each of the components of the system shown in FIG. 9.

CPU SYSTEM: The control computer subsystem 40 is comprised of an embedded microcontroller which supports the computation requirements of the device. It provides timing, interrupt service control, memory management and control of all peripheral devices under program control. Storage of calibration constants and other non-volatile data is supported via a small EEPROM.

EXTERNAL INTERFACE: A serial interface is provided for establishing connection with other subsystems, as well as for testing and manufacturing support. In particular, an embodiment of the present invention can be linked to a pulse oximeter so that the measurement of the various hemoglobin derivatives can be determined independently of co-oximetry and pulse oximetry. The information obtained from the multi-component system of the present invention may be used to further improve the accuracy of the medical device and system of the invention as described in U.S. Ser. No. 09/460,251, which is incorporated by reference herein in its entirety.

Portable and hand-held pulse oximeters are well known in the art. Examples of such pulse oximeters are found in U.S. Pat. No. 4,733, 422, U.S. Pat. No. 5,490,523 and U.S. Pat. No. 5,792,052, all issued to Isaacson et al., and U.S. Pat. No. 5,575,284 issued to Athan and Scharf, which are incorporated herein by reference. Currently marketed hand-held pulse oximeters are produced by BCI International, such as Model BCI 3301, and Model BCI 3303. Other marketed portable pulse oximeters are available from Nonin, such as the Onyx Finger Pulse Oximeter Model, and PaceTech, Inc., such as the Vitalmax 800 plus Model. These patented devices and products are all suitable for use as linked pulse oximeters in the medical device and system of the present invention.

DATA ACQUISITION SUBSYSTEM: The sensor system interfaces to the computer through a number of data acquisition components. Interfaces for analog input (ADC, or analog to digital conversion), analog output (DAC, or digital to analog conversion) and digital IO (input/output) are contained in the subsystem. These subsections connect to the emitter and detector electronics as well as providing support for self diagnostics and system status testing. They are discussed further with their corresponding subsystems.

EMITTER SUBSYSTEM: Light emitting diodes produce output which is essentially proportional to the current through the diode. The emitter drive system provides a precision, high performance bipolar constant current source whose output current is determined by an input reference voltage, which is provided by a digital to analog converter (DAC). Setting the DAC to a given value results in a very precise current being sourced to a LED.

An embodiment of the system of the present invention utilizes six LEDs as emitters. These may be combined via a light-pipe assembly, or through optical fibers, or all dies may be bonded onto one hybrid with a single lens. Whether a LED is active, and at what output level, is determined by program control. Any one of the six emitters of the emitter subsystem may be activated at a precise operating current and for a period determined by the control system.

SENSOR OPTICS: The sensor optics system consists of a block of opaque material 10 which is machined or molded to provide for retention of a sample cell 18 (cuvette) containing the specimen to be analyzed 17 (blood). The block is configured to allow for optical communication with the various emitters and optical detector(s)f which are maintained in optical alignment and project through the active proportion of the sample cell.

DETECTOR SUBSYSTEM: The detector subsystem utilizes a blue enhanced low noise PIN diode as its detector. These devices have been selected as they are known to have good linearity and appropriate characteristics in the visible to near infrared wavelength range. Light falling onto the die of a PIN diode results in a current proportional to the incident luminance. The position of the LED to the PIN diode may be arranged to result in the transmittance, absorbance, reflectance measurement. The PIN diode is connected to a transimpedance amplifier, which has been designed for very high sensitivity, low noise and fast response.

PROGRAMMABLE GAIN AMPLIFIER: The transimpedance amplifier is connected to a programmable gain amplifier, then to one channel of the ADC input multiplexer, from which it is routed to a sample and hold circuit and finally to the analog to digital converter (ADC). The ADC converts the voltage resulting from the detector subsystem to a numerical value, which is then suitable for use by the computer program.

OTHER: In addition to the core functionality described above, there is support for internal test and validation of data, power supply functionality, emitter drive system test circuitry and program data validation.

FIG. 10 illustrates the optical layout of an embodiment of a microspectrophotometer 10 of the invention. This device consists of six compact light sources, namely six LEDs 11, 12, 13, 14, 15, and 16, a sample cell/cuvette 18, six photodetectors 26, 26, 27, 28, 29 and 30, a microprocessor 40 of the CPU system and display 42. The LEDs and photodetectors are mounted inside an opaque black housing. The LEDs are controlled by a programmable constant current source and selection logic which communicate with the microprocessor. The light generated by the LEDs is directed onto the cuvette 18. The cuvette is filled with the sample to be measured. The cuvette is inserted into the housing 10 adjacent the emitters. The light transmitted through the sample filled cuvette to the photodetectors 25, 26, 27, 28, 29 and 30 with peak emission wavelengths at about 500, 525, 555, 568, 612 and 810 nm.

The photodetectors are comprised of PIN photodiodes (such as a Photonic Detectors Inc. PDB-Vb 104). Each photodiode is coupled in the detector subsystem 6 to a corresponding high-speed transimpedance amplifier. The resulting output voltages from each transimpedance amplifier are then connected to the microprocessor 40 via an analog multiplexer and analog to digital converted (ADC) and further calculations are performed.

The following further details the enabling method yielding the portable co-oximeter of the present invention.

1. Summary of the Enabling Technology a) Overall Design and Results

Thus, the co-oximeter of the present invention is generally enabled to be portable by three design characteristics. These may be defined as:
 a) using small optical components that do not require tight controls;
 b) performing the measurement on whole blood; and
 c) using ratiometric calculations.

Of these three design characteristics, it is specifically the use of small optical components that allow the mechanical design and electronics of the co-oximeter to be small enough to be portable. Use of whole blood allows the design to be smaller still.

Typical hemolyzing methods include ultrasonic devices that are large and have high power requirements. If hemolyzing the blood was deemed necessary, a small pump with water and/or other chemicals might be used to lyse the blood and still allow the instrument to be portable.

Temperature control can be designed into embodiments of the co-oximeter within a small amount of real estate but designing methods for temperature compensation allows for a simpler and even smaller mechanical design.

In this device, the procedures for measurement have been developed to accommodate the performance characteristics of the smaller optical components utilized. The method continues to use the laws of optics and the Beer-Lambert Law as do all existing co-oximeters.

It is clear that small optical components alone, such as LEDs having bandwidths from about 7 to 100 nm, would not allow accurate measurements or even have the capability of distinction between hemoglobin derivatives. It is for this reason that co-oximeters of the past have relied upon tightly controlled optical components requiring diffraction gratings, tight bandpass filters, tightly controlled laser diodes and the like as the optical components of choice.

With an understanding of the capabilities of LED technology, however, the current method, device and system were developed by going further back into the history of co-oximetry and looking at the extinction coefficients through a wider bandwidth "filter", in particular a 40 nm bandwidth "filter."

This filter was devised with mathematical equations. Starting with a possible worst case of 40 nm bandwidth light source, an equation was developed to simulate the performance of a 40 nm bandwidth LED. Very simply summarized, the data of the extinction coefficients plotted above were averaged over a 40 nm range. In a linear averaging each point of the new plot would consist of an average of 20 data points from the above plot. This would, of course, be performed by taking a sum of the values at each of the 20 wavelengths totaling the 40 nm bandwidth and dividing the sum by 20. This linear averaging, however, does not simulate the performance of a LED. An LED radiates light at a certain peak wavelength and around that peak wavelength to varying degrees. The point(s) or wavelength range at which 50% of the peak output is known as the center wavelength (CWL) and may be considered the bandwidth of the LED. The shape of the curve dictates the confidence that all the radiated light above 50% intensity will be modeled by a $3^{rd}$ degree polynomial around the peak.

An example of the performance curve of an LED in the 612 nm peak wavelength shows that at 50% intensity the wavelength range is 12 nm. This data was provided by PRP Optoelectronics DIS 390 series 612 nm peak wavelength LED. It should be noted that any peak wavelength, with associated bandwidth and standard deviation may be reduced into an equation and further devised into a "filter" or weighting table to establish working extinction coefficient spectra consistent with the optical components of interest. This may also be accomplished by creation of a "look-up" table.

Superimposing the LED characteristic curves shown in FIG. 2, over the plot of the extinction coefficients of Zwart, et al., yields the plot of FIG. 3. The characteristics of each LED are slightly different, however, the curves seem to overlap even at the ends of their output spectra.

These changes are reflected in the optical spectra shown in FIG. 3. The curves of the above plots shown in the figure greatly differing maxima and isobestic points from those measured by Zwart at a 2 nm bandwidth. These new and different maxima and isobestic points are then used to determine the concentration of the hemoglobin derivatives of interest using larger bandwidth light sources.

A sixth wavelength was also used in order to adjust for the turbidity of a whole blood sample. The wavelength of 722 nm was initially used. Further investigation in the area of turbidity and hematocrit showed that the near infrared wavelengths gave results that were more favorable with respect to hematocrit only over a longer bandwidth. For this reason, 810 nm is now preferred.

It is noteworthy that the invention is developed with a 40 nm bandwidth as an illustration of the worst case scenario. LEDs are readily available in tighter bandwidths of 12–35 nm in the blue, green, yellow and orange ranges and approach 30–50 nm when entering the red to near infrared range as is shown in FIG. 2.

The results rendered from the solution of five simultaneous equations adjusted for turbidity using the 6th wavelength gives good estimation of each concentration of hemoglobin derivative. These same wavelengths may be used in a ratiometric calculation to verify and/or adjust the percentages of each hemoglobin derivative and allow the compensation for environmental factors such as sample temperature, air bubbles and pH.

b) The Ratiometric Refinement

The ratiometric portion of this measurement was developed in the following manner. It was assumed that the effects of any present metHb and sHb would be of low significance. In the case where the metHb and sHb derivatives are low, this is a valid assumption on its own. In addition, the presence of any amount of these derivatives may also be taken into account by using Beer's Lambert's Law:

Using this equation, the contribution of the metHb and sHb may be adjusted for by subtracting the $\epsilon(\lambda)*c*l$ for each of the two derivatives.

The sum of all Hb derivatives may be calculated and representative of the total amount of Hb, both functional and nonfunctional in the blood sample. Physiologically, the tHb is related to the volume percent of red blood cells in the blood sample, hematocrit, by a factor of three when tHb is presented in units of gram % or g/dL. The equation is known as tHb[g/dL]*3=Hct. This may serve as an estimate of hematocrit.

In addition, the measurement of turbidity may directly be related to the amount of red blood cells present in the sample or Hct. Red blood cells act as diffuse reflectors in the visible to near infrared wavelength ranges. By measurement of the transmittance of a blood sample the indirect measurement of absorbance and scattering is accomplished. The absorbance of Hb derivatives in the wavelength ranges of 650 nm to the near infrared (1000 nm) is very low. In this range the measurement of transmittance would then be an indirect measurement of scattering reflectance only. With the direct measurement of HCT and the calculated HCT based on the tHb measurement, both measurements may serve as verification or validation for increased confidence of the measurements of tHb, each Hb derivative or HCT.

The ratiometric method applied to the co-oximeter of the present invention can be used for verification of initial results using 5 distinct absorbance measurements to distinguish 5 distinct hemoglobin derivatives. Specifically the Hb derivatives are COHb, metHb, $O_2Hb$, rHb and sHb. The corresponding peak wavelengths to measure these derivatives are about: 534 nm, 500 nm, 568 nm, 554 nm and 616 nm as shown calculated weighted spectra of FIG. 3. This is based on a methodology that looks at the spectrum of each specific derivative with respect to wavelength assuming a 40 nm bandwidth.

The ratiometric portion of the program was initiated focusing on the three derivatives that have similar optical spectra, specifically COHb, $O_2Hb$ and rHb.

Figure 11:
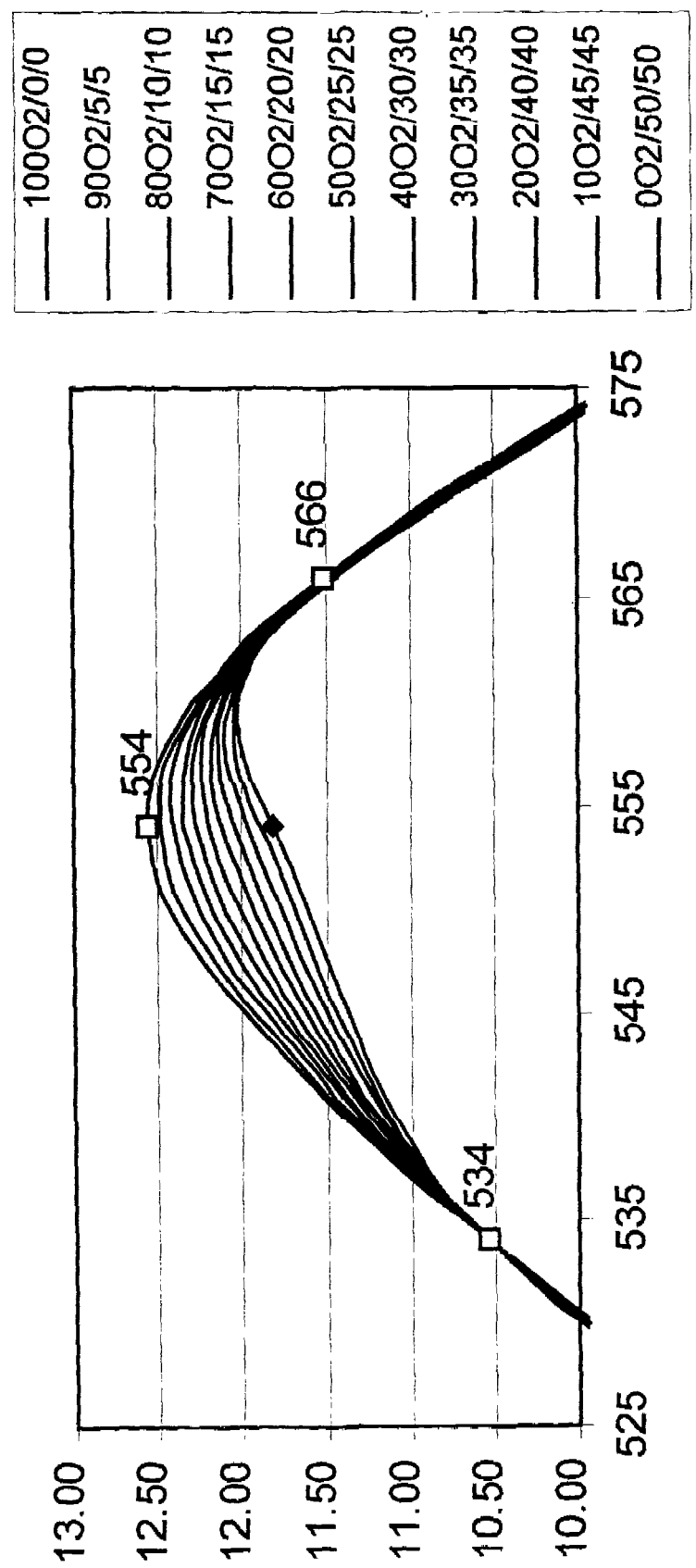
FIG. 11 is a plot of absorbance of a theoretical 40 nm bandwidth as a function of percentage of $O_2Hb$ in combination with COHb and rHb. The amount of metHb and sHb are calculated to be negligible in this plot.

A set of theoretical mixtures of COHb, $O_2Hb$ and rHb were made up consisting of 100% $O_2Hb$, 90% $O_2Hb$ with 5% COHb and 5% rHb, 80%/10%/10% down to 0/50/50. The same was repeated when starting with 100% COHb and again with 100% rHb. These were plotted as a function of wavelength. FIG. 11 shows the resulting plot of percentage of $O_2Hb$ mixtures against wavelength.

It is noteworthy that for mixtures of various percentages of $O_2Hb$ derivative, there is good separation at 554 nm and no separation and good amplitude at 534 nm and 566 nm. In this case, 566 nm or 534 nm may provide information as a reference wavelength absorbance measurement with good amplitude optical spectra but not affected by changing percentages of $O_2Hb$.

Figure 12:
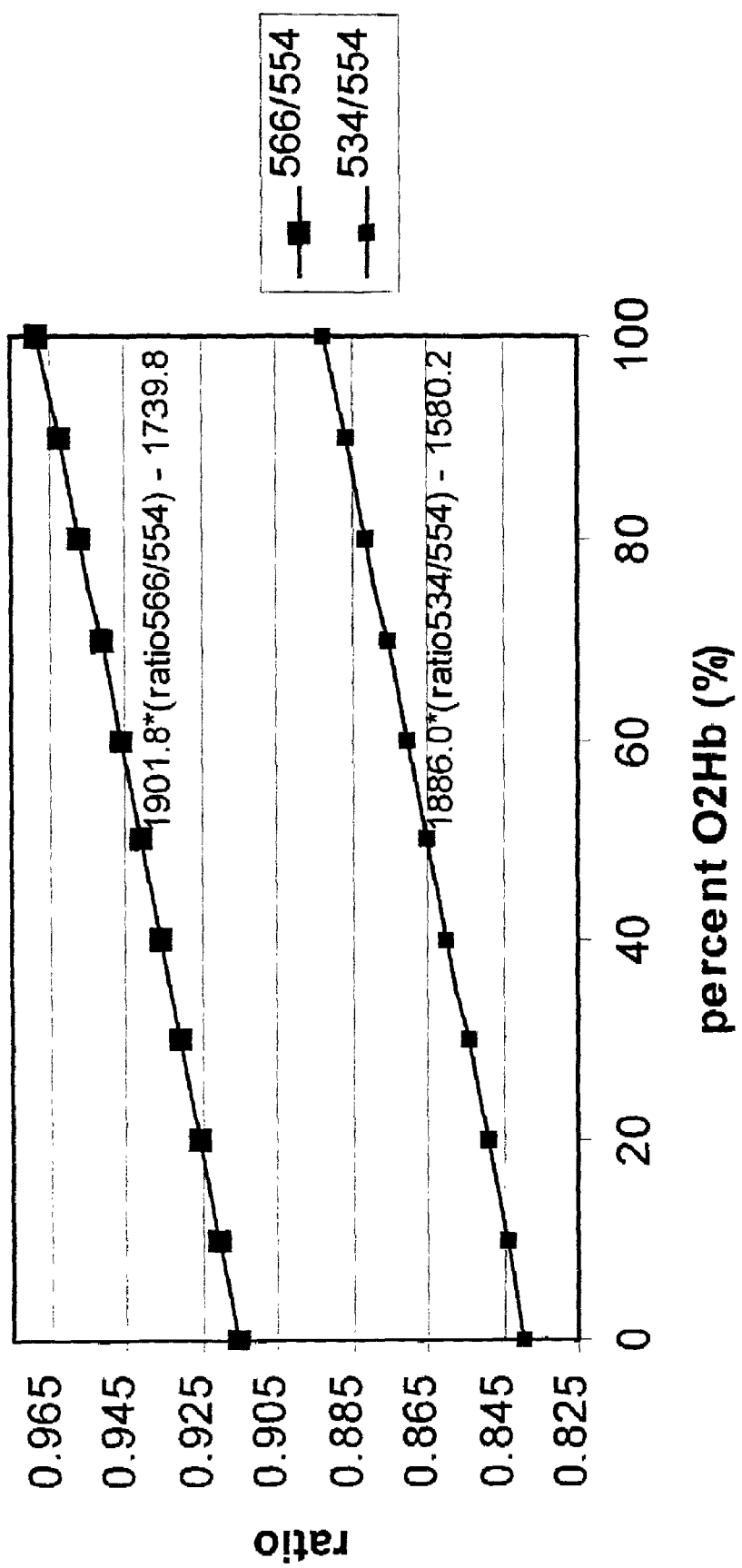
FIG. 12 is a plot of the ratio of absorbance of the theoretical 40 nm bandwidth as a function of percentage of $O_2Hb$ in combination with COHb & rHb. The amount of metHb and sHb are calculated to be negligible in this plot. There are two ratiometric relationships shown in this plot. One relationship may be more accurate than the other depending on the environmental factors.

FIG. 12 represents the ratiometric relationships of the percentages of $O_2Hb$ in combination with rHb and COHb. In all these representations, metHb and sHb have been calculated to be 0%. It is interesting to note that when $O_2Hb$ is the dominating Hb derivative, the most representative in a clinical sense, either ratiometric relationship (abs566 nm/abs554 nm) or (abs534 nm/abs554 nm) will suffice as a measurement.

When rHb is high, however, it is preferred to use the (abs566 nm/abs554 nm) as the rHb has a large response in the 534 nm range. This measurement is less important during clinical use as high concentrations of rHb do not occur in live human blood samples.

In addition, 554 nm may provide information as a measuring wavelength absorbance measurement with good amplitude optical spectra and is highly affected by Hb derivative that is dominating. The absorbance at 554 nm may be described as a function of (Hb derivative mixture, temperature, pH, turbidity, hematocrit, air bubbles, etc.) The absorbance at 566 nm or 534 nm may be described as a function of (temperature, pH, turbidity, hematocrit, air bubbles, etc.)

Therefore when calculating the ratiometric measurement of a measured absorbance/reference absorbance, the values resulting are a function of the Hb derivative mixture only. It should also be noted that this relationship may also be described by polynomial equations of various orders.

By the same methods, evaluations of rHb and COHb may be performed.

The plots of rHb and COHb derivatives also have a linear relationship between a ratiometric measurement and percentage of each derivative.

By using these ratiometric measurements, the percentage of derivative may be calculated and compared to the results received from the original solution using 5 distinct wavelengths. The hemoglobin derivatives of lower percentages may also be calculated using the same equations, however, care must be taken to distinguish which ratiometric relationship to use. The selection of the appropriate ratiometric relationship may be performed in software as part of the electronics.

This comparison may serve as a verification of the initial results and may be further served as an adjustment to run through one or more "iterations" of calculations to increase the accuracy and/or confidence of the calculated derivative concentrations and percentages.

2. Specific Example Using Weighted Spectrophotometric Data

The following is an example of how the method of the present invention can be used to determine the concentration and/or percentages of hemoglobin derivative in a blood sample from a patient. The data from the spectrophotometer is input into a Mathsoft Mathcad program and the resulting calculations compared to the results and printout of the AVL912 Co-Oximeter.

An example of the order in which the measurements are performed and calculated may be done in the following manner.

Choose LED components to be used. Obtain associated output data with respect to peak wavelength and output along its bandwidth (this is usually provided by the manufacturer of the LED)

Using this function or using a look-up table, calculate the extinction coefficient associated with the peak wavelength and bandwidth.

Measure the absorbance at each of the wavelengths.

In the case of whole blood, adjust the absorbance for the turbidity.

Solve simultaneous linear equations using the pathlength of the cuvette, the calculated extinction coefficients and measured adjusted absorbances. This gives the concentration of each hemoglobin derivative.

Sum the individual Hb derivatives resulting in tHb.

Divide each concentration by the tHb resulting in % Hb derivative.

Determine if the resulting percentages are in the High O2Hb, High COHb or High rHb.

Adjust the absorbances of the appropriate wavelengths to subtract the contribution of any metHb and sHb present using Beer-Lambert Law.

Calculate the appropriate ratiometric value based on the dominating Hb derivative.

Solve the linear or polynomial equation resulting in % of dominating Hb derivative.

Repeat, making appropriate adjustments absorbance and/or ratiometric values until the ratiometric and linear equations fall within the desired accuracy.

A mixture of whole bovine blood and AVL Confitest 2 solutions was prepared.

This was done in order to attain a turbid sample with a high % of COHb near to a high clinical level. The AVL Confitest solution has an absorbance that simulates a 95% COHb, which is not clinically relevant.

Figure 13:
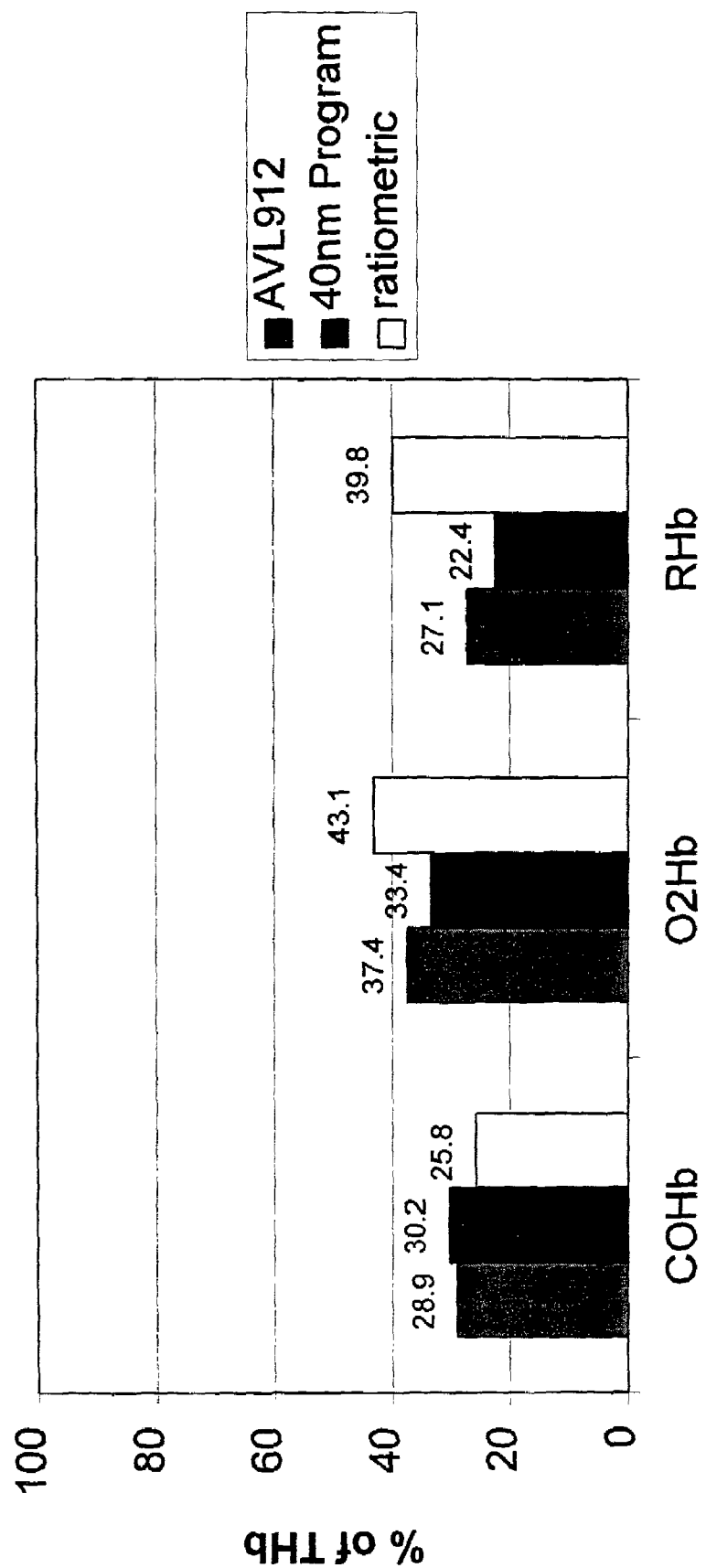
FIG. 13 is a representation of the results for measurements of $O_2Hb$, rHb and COHb in a mixture of Confitest solution and whole bovine blood. The results from the AVL912 are charted along with the results of the spectrophotometer placed through the 40 nm program and Beer-Lambert Law calculations, as well as the same 40 nm data placed through the ratiometric relationship, as described by FIG. 12.

The results are plotted in FIG. 13. The data taken from the AVL912 is plotted with the data from the HP8541A spectrophotometer and placed through the software program simulating a theoretical 40 nm bandwidth LED and through the Beer-Lambert Law. The ratiometric data is calculated using the 40 nm weighted data and taken as a first pass through the ratiometric relationships as described by FIG. 12 and similar. For further refinement, this data may be placed into a feedback loop to repeat until a specified confidence is found.

3. Specific Example Using LED Data

Light Emitting Diodes were received from PRP Optoelectronics. The relative intensity was taken across 100 nm at 1 nm and used to create a weighted lookup table. LEDs were received in the following peak wavelengths: 506, 525, 555, 568, 612 and 810 nm. The LEDs ranged in CWL bandwidth from 12–36 nm as is shown in FIG. 2. $3^{rd}$ degree polynomials were generated that estimated the output of the LEDs that gave 93–99% confidence factors.

Measurements of the AVL Confitest solutions were placed into a sample cuvette and into the device described above, where each LED was mechanically placed on the opposite side of a photodiode. Measurements of transmittance were taken, transferred into absorbance and placed through the Beer-Lambert Law using the weighted extinction coefficients corresponding to the peak wavelengths.

Figure 14:
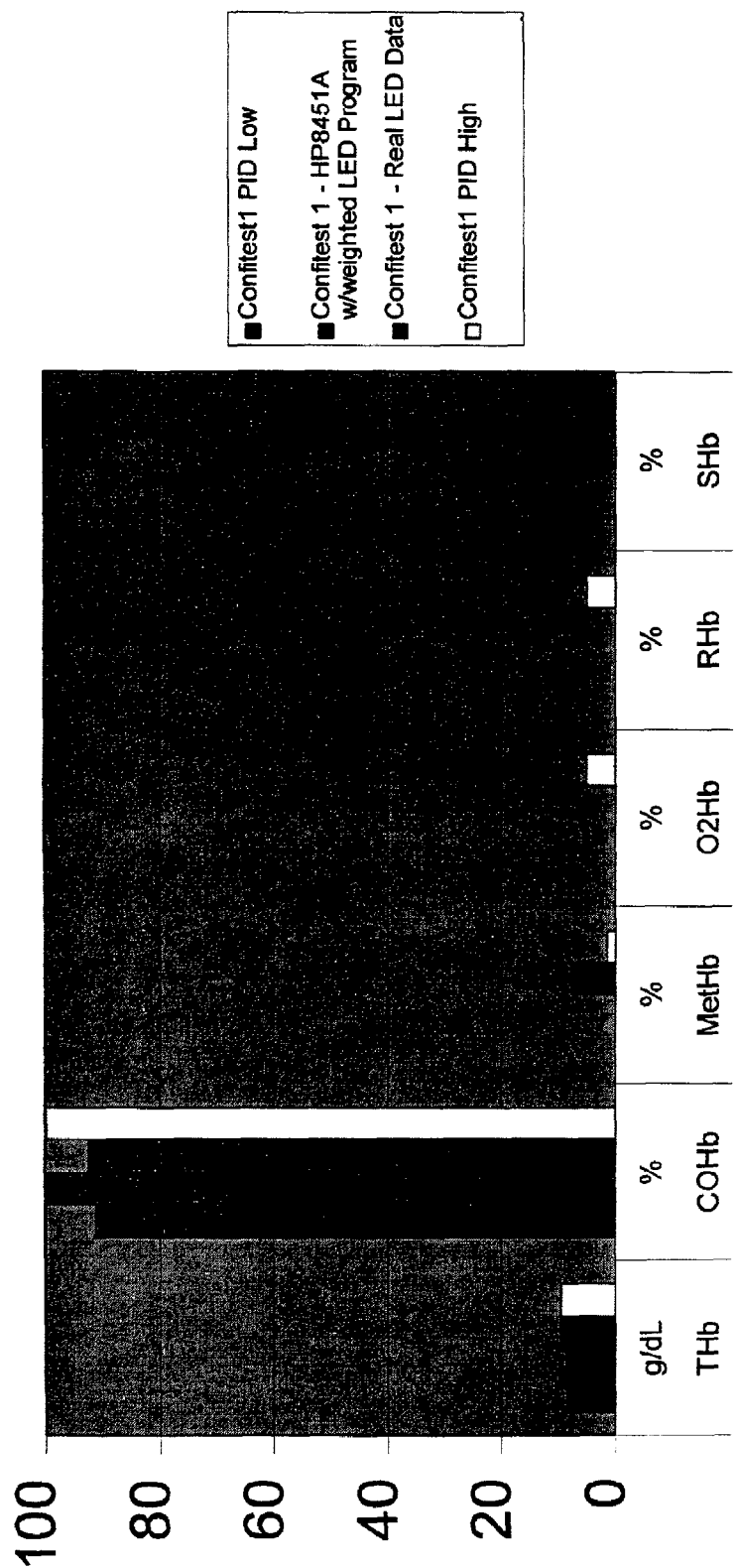
FIG. 14 is a representation of the results for measurements of various hemoglobin derivatives using AVL Confitest Level 1 ff™ solutions (low clinical tHb levels), which are standard solutions that mimic the behavior of the various hemoglobin derivatives, as well as results from real LEDs of the peak wavelengths as labeled on FIG. 2, the results using five distinct wavelengths taken from the spectra generated as in FIG. 4 at 12–36 nm bandwidths of theoretical LEDs using an HP8541A spectrophotometer along with the range for each hemoglobin species from the Confitest Product Insert Datasheet (PID).
Figure 15:
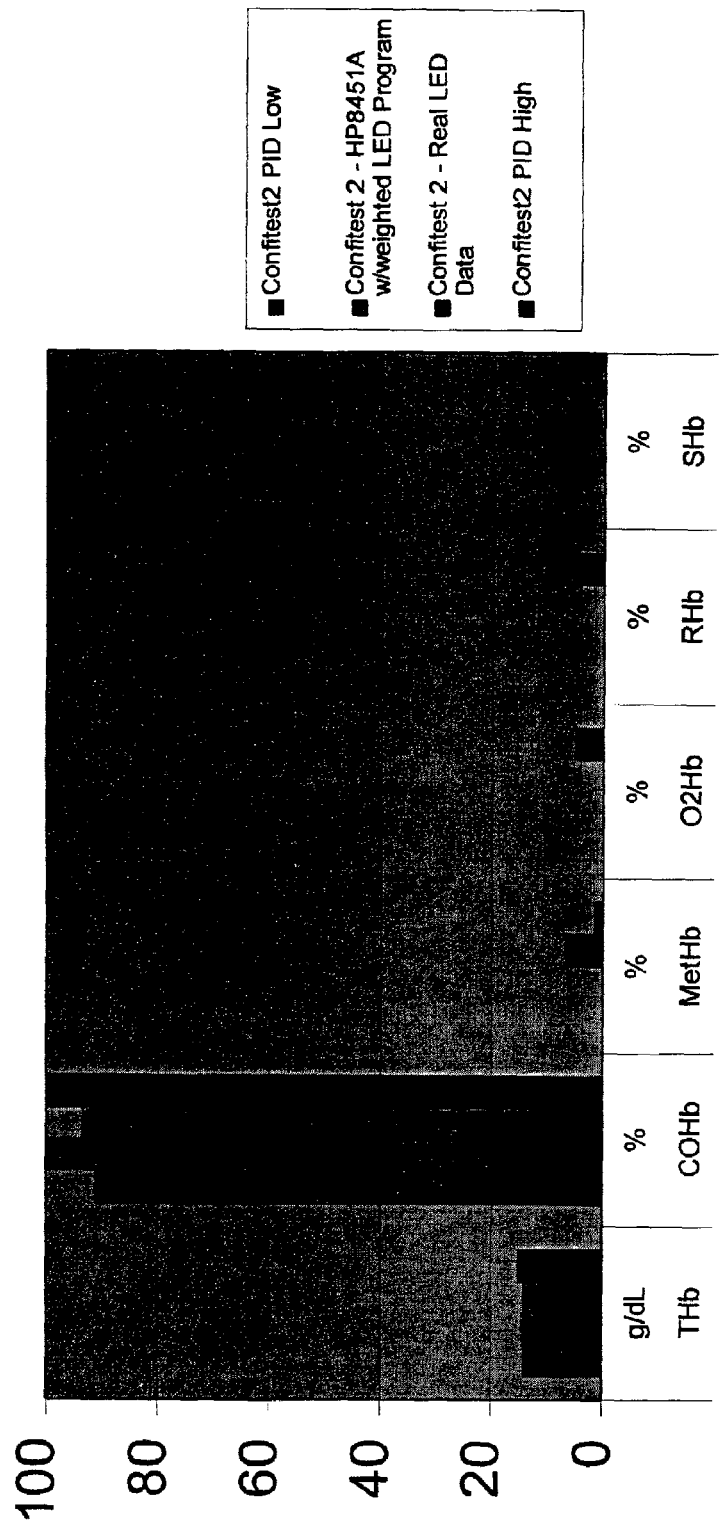
FIG. 15 is a representation of the results for measurements of various hemoglobin derivatives using AVL Confitest Level 1 ff™ solutions (mid clinical tHb levels), which are standard solutions that mimic the behavior of the various hemoglobin derivatives, as well as results from real LEDs of the peak wavelengths as labeled in FIG. 2, the results using five distinct wavelengths taken from the spectra generated as in FIG. 4 at 12–35 nm bandwidths of theoretical LEDs using an HP8541A spectrophotometer along with the range for each hemoglobin species from the Confitest Product Insert Datasheet (PID).
Figure 16:
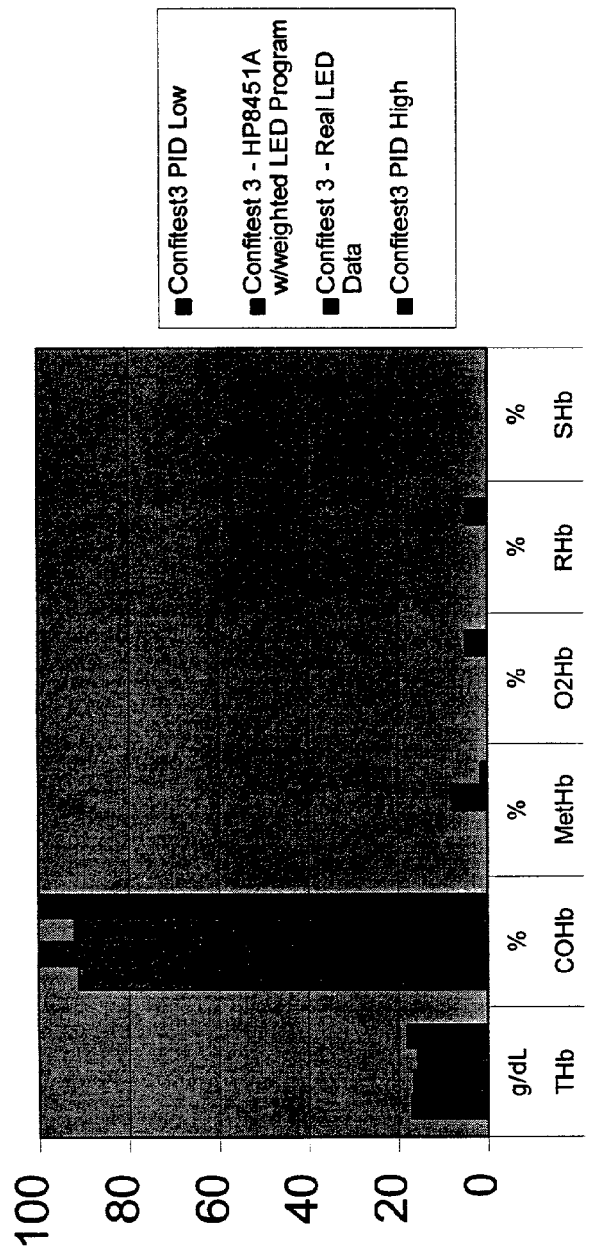
FIG. 16 is a representation of the results for measurements of various hemoglobin derivatives using AVL Confitest Level 3 ff™ solutions (high clinical tHb levels), which are standard solutions that mimic the behavior of the various hemoglobin derivatives, as well as results from real LEDs o the peak wavelengths labeled on FIG. 2, the results using five distinct wavelengths taken from the spectra generated in FIG. 4 at 12–35 nm bandwidths of theoretical LEDs using an HP8451 spectrophotometer along with the range for each hemoglobin species from the Confitest Product Insert Datasheet (PID).

The results were compared to results of the same fluid placed into a similar cuvette and measured with the HP8451 Spectrophotometer. A proprietary software program incorporating the weighted extinction coefficients of the LEDs and Beer-Lambert Law was used and represented as HP8451A with weighted LED program in FIGS. 14, 15 and 16. The same software program replacing the measurements of transmittance from the device for the weighted measurements of the spectrophotometer and are represented as Real LED Data in FIGS. 14, 15 and 16.

The results show similar trending with tHb measurements within the expectation of accuracy stated by the AVL product insert datasheet.

4. Conclusion
  a) The method of starting with the performance of the optical components to adjust the extinction coefficient data can be used to perform the Beer-Lambert Law solving 5 simultaneous equations to result in concentration data of Hb derivatives in a whole blood sample.
  b) Using a near infrared absorbance can be used as an adjustment for turbidity.
  c) A ratiometric relationship with % Hb derivative can be used to verify or increase confidence and accuracy of the concentrations arrived at using the Beer-Lambert law.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

The above description of the invention applies to embodiments of the system, device and methods of the invention whether or not explicitly stated.

Any element in a claim that does not explicitly state "means" for performing a specified function or "step" for performing a specified function, should not be interpreted as a "means" or "step" clause as specified in 35 U.S.C. §112.

The abstract is submitted only to comply with 37 C.F.R. 1.72. The language in the abstract should not be used to interpret the scope of the claims. Further, the abstract is not to be used in any manner other than to assist the Patent and Trademark Office and the general public in determining the gist of the invention.

What is claimed is:

1. A medical device for measuring the concentration and/or percentages of one or more hemoglobin derivatives in a blood sample taken from a patient comprising;
  a) a housing;
  b) a holder for the blood sample contained within the housing;
  c) a light generating apparatus, contained within the housing comprising at least one compact light source emitting light in the visible region of the spectrum or at least one polychromatic light source and at least one light filter for separating the light from the polychromatic light source into distinct bandwidths along the visible spectrum; wherein the number of light sources or filters in the visible region of the electromagnetic spectrum is less than or equal to the number of hemoglobin derivatives to be measured and wherein the compact light source(s) or light filter(s) have bandwidths of about 7–50 nanometers;
  d) a light receiving apparatus contained within the housing comprising at least one light detector receiving light for determining one or more absorbance values of the blood sample at one or more wavelengths within the bandwidth of each light source or filter in the visible region of the spectrum; and
  e) a microprocessor for determining the concentration of each hemoglobin derivative from the measured absorbance values.

2. The medical device of claim 1, wherein the optimal wavelength for determining the absorbance value(s) for a hemoglobin derivative depends on the characteristics of the compact light source and/or optical filter used in the device.

3. The medical device of claim 1, wherein the overall size of the device is sufficiently small so as to be hand-held.

4. The medical device of claim 1, wherein the portable device weighs less than about 50 pounds.

5. The medical device of claim 1, wherein at least one light source emits light ranging from about 450 nanometers to about 700 nanometers.

6. The medical device of claim 1, wherein the compact light sources comprise light emitting diodes, light emitting lasers, a polychromatic light or combinations thereof.

7. The medical device of claim 1, wherein the light receiving source(s) comprise photo detectors, photo diodes, pin diodes, photo transistors, CCD arrays, photo multiplier tubes or combinations thereof.

8. The medical device of claim 1, wherein the blood sample comprises hemolyzed blood.

9. The medical device of claim 1, further comprising at least one light source emitting light in the high visible to infra red region of the electromagnetic spectrum.

10. The medical device of claim 9, wherein the blood sample comprises non-hemolyzed blood.

11. The medical device of claim 9, wherein the light source emits light in the range of about 650 nanometers to about 1000 nanometers.

12. The medical device of claim 9, wherein the light receiving detector lies on the same plane as the plane used to measure the reflectance of the blood sample.

13. The medical device of claim 9, wherein the absorbance and/or reflectance is used to measure and/or calculate the hematocrit and/or to measure all hemoglobin derivatives as total hemoglobin of non-hemolyzed blood sample.

14. The medical device of claim 1, comprising at least two compact light sources for distinguishing two or more hemoglobin derivatives.

15. The medical device of claim 1, comprising at least three compact light sources for distinguishing three or more hemoglobin derivatives.

16. The medical device of claim 1, comprising at least five compact light sources for distinguishing five or more hemoglobin derivatives.

17. The medical device of claim 1, comprising at least three compact light sources for distinguishing two or more hemoglobin derivatives, wherein one light source emits light in the high visible to infra red region of the electromagnetic spectrum.

18. The medical device of claim 1, wherein the hemoglobin derivatives to be measured are oxyhemoglobin, reduced hemoglobin, partial hemoglobin, carboxyhemoglobin, methemoglobin, fetal hemoglobin and/or sulfhemoglobin.

19. The medical device of claim 1, wherein the device further yields values for total hemoglobin, hematocrit, oxygen saturation, fractional oxygen saturation, oxygen content and/or oxygen capacity.

20. The medical device of claim 1, wherein the microprocessor comprises software capable of validating and/or adjusting the measured concentrations and/or percentages of hemoglobin derivatives by use of one or more ratiometric curves.

21. The medical device of claim 1, wherein the device is battery powered.

22. The medical device of claim 20, wherein the ratiometric calibration curves, comprise known ratios of absorbance values taken from absorbance spectra comprising more than one hemoglobin derivative.

23. The medical device of claim 20, wherein the ratiometric curves comprise spectral data for combinations of two or more hemoglobin derivatives at various known concentrations.

* * * * *